United States Patent [19]

Umezawa et al.

[11] 4,147,778

[45] Apr. 3, 1979

[54] ANTIBIOTIC BAUMYCIN COMPLEX AND COMPONENTS THEREOF

[75] Inventors: Hamao Umezawa; Tomio Takeuchi; Masa Hamada; Masaaki Ishizuka; Hiroshi Naganawa, all of Tokyo; Toshikazu Oki, Kamakurashi; Taiji Inui, Chigasakishi, all of Japan

[73] Assignee: Zaidan Hojin Biseibutsu Kagaku Kenkyu Kai, Tokyo, Japan

[21] Appl. No.: 797,201

[22] Filed: May 16, 1977

[30] Foreign Application Priority Data

May 31, 1976 [JP] Japan ................... 51-63810

[51] Int. Cl.² ............. A61K 31/71; C07H 15/24
[52] U.S. Cl. ................. 424/181; 195/80 R; 424/180; 536/4; 536/17; 536/53
[58] Field of Search ............... 536/17 A, 17, 22; 424/181

[56] References Cited

U.S. PATENT DOCUMENTS 3,803,124  4/1974  Arcamone et al. ............... 536/17 A
4,039,663  8/1977  Arcamone et al. ............... 536/17 A

OTHER PUBLICATIONS

Gottlieb et al., "Antibiotics", vol. 1, 1967, pp. 190-210.

Primary Examiner—Johnnie R. Brown
Attorney, Agent, or Firm—David M. Morse

[57] ABSTRACT

A novel anthracycline antibiotic complex designated herein as baumycin complex is produced by fermentation of a baumycin-producing strain of Streptomyces, e.g. *Streptomyces coeruleorubidus* ME 130-A4 (FERM-P3540, ATCC 31276). The complex and four bioactive components thereof designated baumycin $A_1$, $A_2$, $B_1$ and $B_2$ are useful as antibacterial and antitumor agents.

14 Claims, 16 Drawing Figures

NMR SPECTRUM OF BAUMYCIN A₂ (100 MHz IN CDCl₃, INTERNAL REFERENCE: TMS)

ULTRAVIOLET AND VISIBLE ABSORPTION SPECTRA OF BAUMYCIN $B_1$

ULTRAVIOLET AND VISIBLE ABSORPTION SPECTRA OF BAUMYCIN B₂

CURVE 1 – IN METHANOL
CURVE 2 – IN 0.1N HCl-METHANOL
CURVE 3 – IN 0.1N NaOH-METHANOL

FIG. 11 INFRARED ABSORPTION SPECTRUM OF BAUMYCIN $B_2$ IN KBr

FIG. 12 NMR SPECTRUM OF BAUMYCIN $B_2$
(100 MHz IN $CDCl_3$ + $CD_3OD$, INTERNAL STANDARD: TMS)

m/e 674 m/e 674

ANTIBIOTIC BAUMYCIN COMPLEX AND COMPONENTS THEREOF

BACKGROUND OF THE INVENTION

1. Field of the Invention

This invention relates to new anthracycline antibiotics, to their production and recovery, and to their therapeutic use.

2. Description of the Prior Art

A number of anthracycline glycosides have been described in the literature. Among them, daunomycin and adriamycin are particularly being watched with keen interest in the field of cancer chemotherapy and have already been applied clinically for human cancers. Preparation of adriamycin by fermentation of *S. peuceticus var. caesius* is disclosed in U.S. Pat. No. 3,590,028. Chemical conversion of daunomycin to adriamycin is taught in U.S. Pat. No. 3,803,124. Daunomycin (produced by fermentation of *S. peuticus* in U.K. 1,003,383) may be the same as Rhone-Poulenc's 13,057 R.P. (formerly rubidomycin and now daunoribicin: see U.K. Pat. Nos. 985,598, 1,188,262 and 1,241,750 and U.S. Pat. No. 3,616,242) and is probably identical to Ciba's danubomycin disclosed in U.S. Pat. No. 3,092,550 and U.K. Pat. No. 901,830. See also U.S. Pat. No. 3,686,163 on dihydrodaunomycin. Cinerubin A and Cinerubin B, glycosides having $\epsilon$-pyrromycinone, are disclosed in U.K. Pat. No. 846,130 [see also U.S. Pat. No. 3,864,480 and Keller-Schierlein, et. al., Antimicrobial Agents and Chemotherapy, page 68 (1970) and Chemical Abstracts, 54, 1466i (1960)]. The anthracycline glycoside carminomycin described in J. Antibiotics 27:254–259 (1974), in West German Specification No. 2,362,707 and in J. Amer. Chem. Soc. 97 (20):5955–5956 (1975) has been reported to be active in several animal tumor systems. The antibiotic pyrromycin disclosed in Chem. Ber. 92:1904–1909 (1959) contains an aglycone $\epsilon$-pyrromycinone and an amino sugar rhodosamine. For further illustrative and summary disclosures of anthracycline antibiotics see Index of Antibiotics from Actinomycetes, Hamao Umezawa, Editor-in-Chief, University Park Press, State College, Pennsylvania, U.S.A. (1967) as follows:

| Antibiotic | Page Number |
|---|---|
| Aklavin | 111 |
| Cinerubin A | 220 |
| Cinerubin B | 221 |
| Danubomycin | 242 |
| Daunomycin | 243 |
| Pyrromycin | 524 |
| Rhodomycin A, B | 561 |
| Rubidomycin | 574 |

The textbook Antibiotics, Vol. 1, Mechanism of Action, edited by David Gottlieb and Paul D. Shaw, Springer-Verlag New York, Inc., N.Y., N.Y. (1967) at pages 190–210 contains a review by A. DiMarco entitled Daunomycin and Related Antibiotics. Information Bulletin, No. 10, International Center of Information of Antibiotics, in collaboration with WHO, December 1972, Belgium, reviews anthracyclines and their derivatives.

SUMMARY OF THE INVENTION

This invention relates to new anthracycline glycoside antibiotics, to processes for their preparation, to pharmaceutical compositions containing them and to the use of such antibiotics or compositions in the treatment of bacterial infections and in the inhibition of tumors in experimental animals. More particularly, it relates to a novel anthracycline glycoside complex designated herein as baumycin complex and to the individual bioactive components of said complex designated baumycin $A_1$, $A_2$, $B_1$ and $B_2$. The complex and above-mentioned components are produced by cultivating a baumycin-producing strain of Streptomyces, most preferably *Streptomyces coeruleorubidus* ME 130-A4 (FERM-P3540, ATCC 31276), in an aqueous nutrient medium containing assimilable sources of carbon, nitrogen, inorganic salts and other factors necessary for the growth of the microorganism under submerged aerobic conditions until a substantial amount of baumycin is produced by said microorganism in said culture medium and, optionally, recovering the baumycin from the culture medium. Baumycin $A_1$, $A_2$, $B_1$ and $B_2$ may be recovered and separated by extraction of the whole fermentation broth, with or without the separation of mycelium, or by extraction from mycelium followed by separation and isolation of the component antibiotics by standard column chromatographic procedures. Baumycin complex and its component anthracycline glycosides, i.e. baumycin $A_1$, $A_2$, $B_1$ and $B_2$, inhibit the growth of gram-positive bacteria and inhibit the growth of various animal tumors.

This invention also embraces baumycin complex and its components, baumycin $A_1$, $A_2$, $B_1$ and $B_2$, as crude solids, as purified solids, as their non-toxic acid addition salts and as complexes with deoxyribonucleic acid.

DETAILED DESCRIPTION

Figure 1:
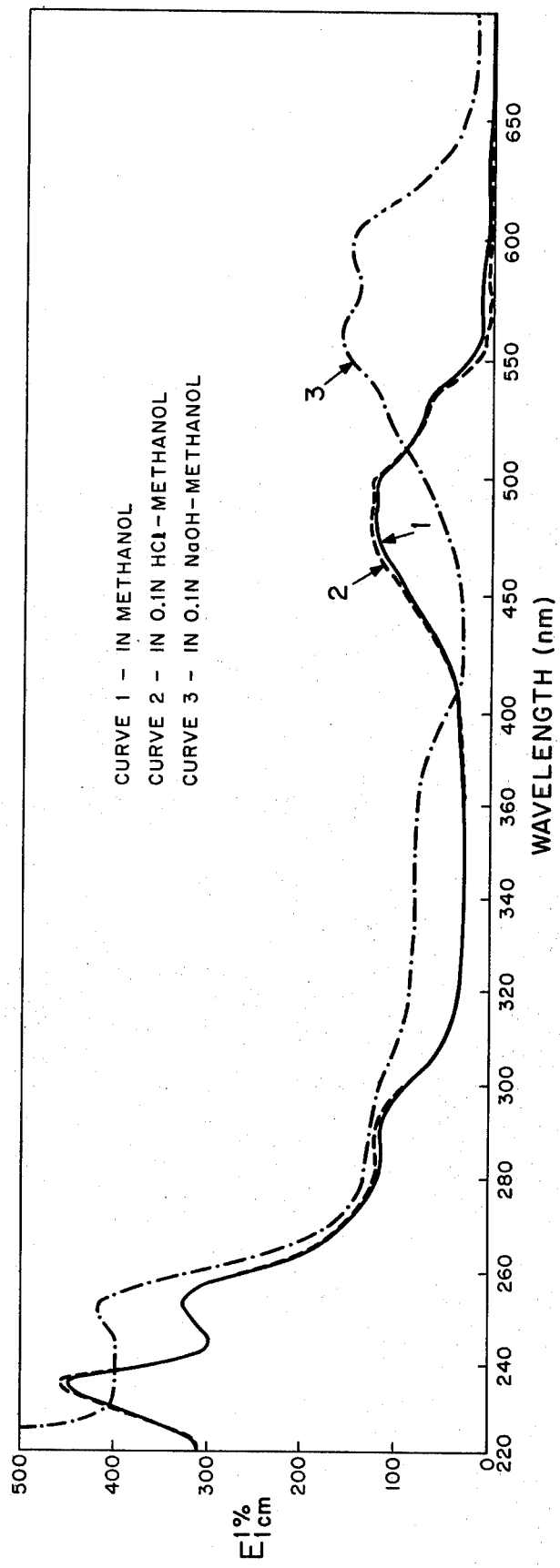
FIG. 1 shows the ultraviolet and visible light absorption spectrum of baumycin $A_1$ in methanol.

The present invention provides the novel anthracycline glycosides of the general formula

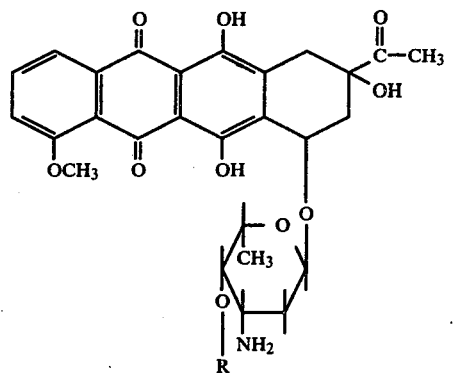

wherein R represents

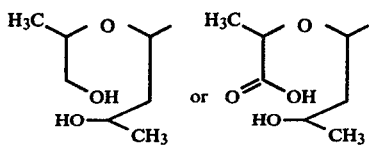

and the non-toxic acid addition salts and complexes thereof with deoxyribonucleic acid.

The compounds of formula I are components of a fermentation-produced anthracycline complex designated herein as baumycin complex. Baumycin complex thus comprises the anthracycline glycosides of the formula

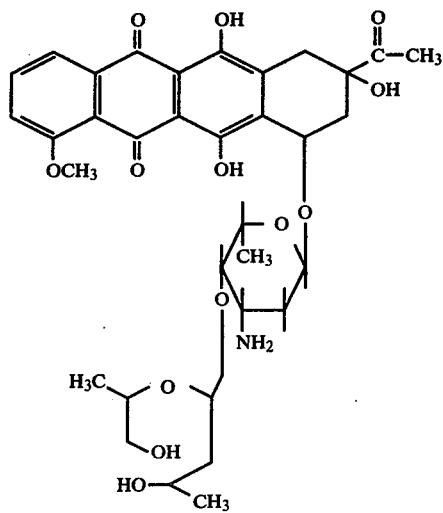

designated baumycin A and the anthracycline glycosides of the formula

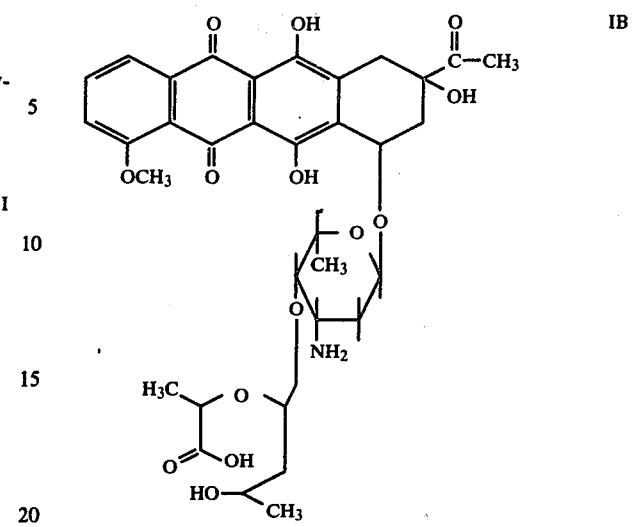

designated baumycin B. It has been established that baumycin A and B can each be separated into two bioactive stereoisomers and thus, formula IA above represents the isomers baumycin $A_1$ and $A_2$ while formula IB represents baumycin $B_1$ and $B_2$. As used herein the term baumycin means the antibiotic comprising at least one of baumycin $A_1$, $A_2$, $B_1$ and $B_2$.

The Microorganism

The compounds of the present invention are produced by fermentation of various baumycin-producing strains of Streptomyces including several known daunomycin-, adriamycin- and carminomycin-producing strains such as *Streptomyces peuceticus subsp. carneus* ATCC 21354, *Streptomyces coeruleorubidus* ATCC 13740, *Streptomyces peuceticus subsp. caestus* NRRL B-5337, *Streptomyces peuceticus* NRRL B-3826 and *Streptomyces coeruleorubidus* NRRL B-3045.

An especially preferred baumycin-producing strain has been isolated by the present inventors from a soil sample collected at the Institute of Microbial Chemistry, Osaki, Tokyo, Japan and designated strain ME 130-A4. Cultures of this strain have been deposited in the American Type Culture Collection, Rockville, Maryland and in the Fermentation Research Institute, Japan, and added to their permanent collections of microorganisms as ATCC 31276 and FERM P-3540 respectively.

Strain ME 130-A4 has the following properties:

(1) Morphological properties:

Under microscope, open spirals and hooks are observed to develop well from branched substrate mycelia. No whorls, and mature spore chain is moderately long with more than ten spores. The spores measure 0.6 to 0.8 μ × 1.0 to 1.2 μ and their surface is spiny.

(2) Growth on various media:

The description in parenthesis follows the color standard "Color Harmony Manual" published by Container Corporation of America, U.S.A.

(a) On glycerol-asparagine agar (ISP medium No. 5), incubated at 27° C.: Pale reddish yellow to dark red (4 ic, Pastel orange to 6½ nc, Catchup) growth; light gray (17 ge, Dusty Aqua Blue to 19 fe, Aqua Gray) aerial mycelium; light reddish yellow soluble pigment.

(b) On sucrose-nitrate agar, incubated at 27° C.: Pale reddish yellow, pale red to dark red (6½ le, Cedar)

growth; slight white aerial mycelium; slight dark red soluble pigment.

(c) On glucose-asparagine agar, incubated at 27° C.: Colorless, pale yellow to pale orange growth; slight white to light gray aerial mycelium then becoming abundant after 14 days incubation; no soluble pigment.

(d) On starch-inorganic salts agar (ISP medium No. 4), incubated at 27° C.: Pale yellowish brown to pale reddish yellow growth; light gray (19 dc, Aqua Gray) aerial mycelium; no soluble pigment.

(e) On tyrosine agar (ISP medium No. 7), incubated at 27° C.: Grayish red brown to brown (4 ni, Chestnut Brown) growth; blue white to light blue (19 dc, Aqua Gray) aerial mycelium; dark brown soluble pigment.

(f) On nutrient agar, incubated at 27° C.: Yellowish brown growth; white aerial mycelium; brown soluble pigment.

(g) On yeast extract-malt extract agar (ISP medium No. 2), incubated at 27° C.: Dull orange (5 ne, Tile Red) growth; light gray (19 fe, Aqua Gray) aerial mycelium; slight brown soluble pigment.

(h) On oatmeal agar (ISP medium No. 3), incubated at 27° C.: Colorless to pale orange growth; light gray (19 fe, Aqua Gray) aerial mycelium; no soluble pigment.

(i) On glycerol-nitrate agar, incubated at 27° C.: Colorless to pale orange growth; white to light gray aerial mycelium; no soluble pigment.

(j) On starch agar, incubated at 27° C.: Light orange growth; white to light gray aerial mycelium, which is faint for 14 days incubation; slight pale orange soluble pigment.

(k) On calcium malate agar, incubated at 27° C.: Colorless, pale orange to dull orange growth, white to light gray (17 ge, Dusty Aqua Blue) aerial mycelium: slight pink soluble pigment.

(l) On cellulose, incubated at 27° C.: Colorless growth; white to dull blue green aerial mycelium; no aerial mycelium.

(m) On gelatin stab, incubated at 20° C.: Slight yellowish brown growth; no aerial mycelium, slight brown soluble pigment.

(n) On glucose-peptone-gelatin stab, incubated at 27° C.: Pale yellowish brown to yellowish brown growth; slight white aerial mycelium; dark brown soluble pigment.

(o) On skimmed milk, incubated at 27° C.: Pale yellowish brown, yellowish brown to pale red growth; slight white aerial mycelium; brown soluble pigment.

(3) Physiological properties:

(a) Growth temperature was examined on glucose-asparagine agar at 20°, 24°, 27°, 30°, 37° and 50° C. and optimal temperature is about 30° to 37° C.

(b) Gelatin liquefaction on 15% gelatin stab at 20° C. and on glucose-peptone-gelatin stab at 27° C.: On the former medium, gelatin liquefaction was observed weakly after 20 days incubation, but on the latter liquefaction began weakly or moderately after 14 days incubation.

(c) Starch hydrolysis on starch-inorganic salts agar and on starch agar at 27° C.: Strong hydrolysis was observed after 3 days incubation on the former medium and after 5 days incubation on the latter medium.

(d) Peptonization and coagulation of skimmed milk at 37° C.: Weak to moderate peptonization began after 7 days incubation and finished coagulation on around 10 to 14 days.

(e) Melanin formation on tryptone-yeast extract broth (ISP medium No. 1), on peptone-yeast extract ferrous agar (ISP medium No. 6) and on tyrosine agar (ISP medium No. 7) at 27° C.: Positive on all media.

(f) Utilization of carbohydrates of Pridham-Gottlieb basal medium (ISP medium No. 9), incubated at 27° C.: Abundant growth with glucose, L-arabinose, D-xylose, sucrose, rattinose.

(g) Liquefaction of calcium malate on calcium malate agar at 27° C.: Strong to moderate liquefaction around the growth was observed after 3 days incubation.

(h) Nitrate reduction on peptone water containing 1% sodium nitrate (ISP medium No. 9), incubated at 27° C.: Negative. Summarizing the above characteristics of No. ME 130-A4, the strain belongs to the genus Streptomyces. Aerial mycelium forms open spirals, but no whorls. The spore surface is spiny. The growth on various media is found to be pale orange to dull red and aerial mycelium is light gray. Slight pale orange soluble pigment is produced. Melanin formation is positive. Proteolytic action is weak to moderate and starch hydrolysis is strong. Among known species of Streptomyces, strain No. ME 130-A4 resembles *Actinomyces coeruleorubidus* based on the above-mentioned properties. (Reference 1: International Journal of Systematic Bacteriology, 18, 312, 1968, Ref. 2: G. F. Gause, Zur Klassifizierung der Actinomyceten, p. 98 Veb. Guotab Fischer Verlag Jena, 1958).

Strain ME 130-A4 and *Act. coeruleobidus* ISP 5145 were compared by parallel cultures. The results are as follows:

|  | ME 130-A4 | Act. coeruleorubidus ISP 5145 |
| --- | --- | --- |
| Spirals | positive | positive |
| Spore surface | spiny | spiny |
| Aerial mycelium | light gray | light gray |
| Growth | pale orange dull red | pale yellowish brown to dull red |
| Melanin formation |  |  |
| ISP medium No. 1 | positive | positive |
| ISP medium No. 6 | positive | positive |
| ISP medium No. 7 | positive | positive |
| Starch hydrolysis | positive | positive |
| Coagulation of milk | positive | positive |
| Peptonization of milk | positive | positive |
| Liquefaction of gelatin | positive | positive |
| Nitrate reduction | negative | positive |
| Utilization of carbohydrates |  |  |
| Glucose | positive | positive |
| L-Arabinose | positive | positive |
| D-Xylose | positive | positive |
| D-Fructose | positive | positive |
| Sucrose | positive | positive |
| Inositol | positive | positive |
| L-Rhamnose | positive | positive |
| Raffinose | positive | positive |
| D-Mannitol | positive | positive |
| Optimal temperature for growth | around 37° C. | around 37° C. |
| Antibiotics produced | Baumycin Daunomycin | Rubidomycin (Daunomycin)* |

*Reference, Jorunal of Pharmaceutical Science 56, 1691 p, 1967.

From the results, it can be seen that the present strain ME 130-A4 agrees very closely with *Actinomyces coeruleorubidus* in morphological and physiological properties. There is only a little difference in the color of the growth, in which the ME 130-A4 strain is a little more red than *Act. coeruleorubidus*.

According to reference 2, nitrate reduction by *St. coeruleorubidus* is variable depending upon the strain of this species. Thus, strain No. ME 130-A4 can be identified as a new strain of *Streptomyces coeruleorubidus*.

Since the Streptomyces are easily mutatable naturally or artificially, *S. coeruleorubidus* No. ME 130-A4 and the other baumycin-producing Streptomyces of the present invention include the typical strains described above and all natural and artificial baumycin-producing variants and mutants thereof.

Production of Baumycin

Production of the compounds of the present invention is carried out by cultivating a baumycin-producing strain of Streptomyces in a conventional aqueous nutrient medium containing known nutritional sources for actinomycetes, i.e. sources of carbon, nitrogen and inorganic salts. Submerged aerobic culture is preferably employed for the production of substantial amounts of baumycin, just as for other antibiotics. The general procedures used for the cultivation of other actinomycetes are applicable to the cultivation according to this invention. The medium preferably contains commercially available carbon sources such as glycerol, glucose, starch, dextrin, sucrose, maltose, oils, fats and the like in either purified or crude state and commercially available nitrogen sources such as soybean powder, yeast extract, peptone, cotton seed powder, dried yeast, corn steep liquor or inorganic salts such as ammonium sulfate, sodium nitrate or ammonium chloride. Inorganic salts such as sodium chloride, potassium chloride or phosphates are preferably used and there may also be added, if necessary, trace metals and defoamers such as Adekanol (Trademark, Asahi Denka Ind. Co.) or silicone (Trade mark, Shinetsu Chem. Ind. Co.). The culture temperature should be in the range of about 20°-35° C., preferably about 25°-30° C. Production of baumycin in the culture broth reaches a maximum after 3 to 7 days in either shake flask or submerged aerobic fermentation with aeration and agitation provided as in the examples shown below.

Separation and Isolation of Baumycin Components

The compounds, baumycin, in the present invention can be recovered from the culture broth and separated from each other by the following procedures.

Baumycin produced by fermentation exists intracellularly as well as extracellularly, but is found mainly in the mycelium. To recover baumycin complex from the culture broth, the broth may be filtered and the filtrate then extracted with a water-immiscible organic solvent such as ethyl acetate, butyl acetate, chloroform or n-butanol. Baumycin in the mycelium can be recovered by extraction with an organic solvent such as chloroform, acetone, n-butanol, methanol, ethanol, ethyl acetate or methyl ethyl ketone or an aqueous solution of an organic or inorganic acid such as hydrochloric acid, sulfuric acid or acetic acid. Alternatively, baumycin can be extracted directly from the culture broth by the above-mentioned extraction procedures without prior separation of the mycelium. After concentrating in vacuo, the baumycin extracts may be re-extracted with a water-immiscible organic solvent at a pH between 7 and 9 and the baumycin then dissolved into an acidic aqueous solution having a pH <4. Baumycin in said acidic aqueous solution is then re-extracted with an organic solvent after adjustment to a weakly basic pH. By repeating the above procedures as necessary, baumycin complex can be prepared in a purified form. As an alternative to using a solvent extraction recovery method or in combination with such a method, baumycin may be recovered from the culture broth by column chromatography using adsorbents such as activated carbon, alumina, silicic acid, or a modified dextran such as that commercially available under the trade name Sephadex LH-20 (Pharmacia Fine Chemical Co., New York, New York), countercurrent distribution or liquid chromatography using suitable organic solvents. Active extracts obtained by such methods are concentrated under reduced pressure and obtained as the crude red powder of baumycin complex.

To obtain the individual baumycin components $A_1$, $A_2$, $B_1$ and $B_2$ from the baumycin complex, further purification and separation may be carried out using such standard separation techniques as column chromatography using various adsorbents such as silicic acid, modified dextrans (e.g. Sephadex LH-20), weakly acidic ion-exchange resins or activated carbon, countercurrent distribution or liquid chromatography using suitable organic solvents, or a combination of one or more of the above-mentioned processes. As an example of a suitable separation procedure, baumycin complex may be dissolved in a small amount of chloroform, subjected to column chromatography over silicic acid and then eluted with a suitable organic solvent, e.g. chloroform-methanol, to give baumycin components $A_1$, $A_2$, $B_1$ and $B_2$. The active eluates are separated, concentrated under reduced pressure and the baumycin components individually purified by chromatography over Sephadex LH-20. After concentration of the active eluates, baumycin $A_1$, $A_2$, $B_1$ and $B_2$ may be obtained in purified crystalline form by recrystallization from a suitable organic solvent.

Physicochemical Properties of Baumycin Components

The physicochemical properties of baumycin $A_1$, $A_2$, $B_1$ and $B_2$ are as follows:

| Baumycin | $A_1$ | | | | $A_2$ | | | |
|---|---|---|---|---|---|---|---|---|
| Appearance | Weakly basic amorphous red powder | | | | | | | |
| Elementary analysis | C | H | N | O | C | H | N | O |
| Found | 59.85 | 6.65 | 2.04 | 29.83 | 60.27 | 6.72 | 2.31 | 29.52 |
| Calcd. | 60.61 | 6.43 | 2.08 | 30.88 | 60.61 | 6.43 | 2.08 | 30.88 |
| Empirical formula | $C_{34}H_{43}NO_{13}$ | | | | | | | |
| Molecular weight | 673.7 | | | | | | | |
| Melting point (° C.) | 182–185 | | | | 185–189 | | | |
| Specific rotation $[\alpha]_D^{20}$ | + 150° | | | | + 135° | | | |
| | ($CHCl_3$, C = 0.1) | | | | | | | |
| Solubility | Soluble in acidic water, DMSO, methylcellosolve, methanol, ethanol, n-propanol, n-butanol ethyl acetate, butyl acetate, acetone, methyl ethyl ketone, methylene | | | | | | | |

Figure 2:
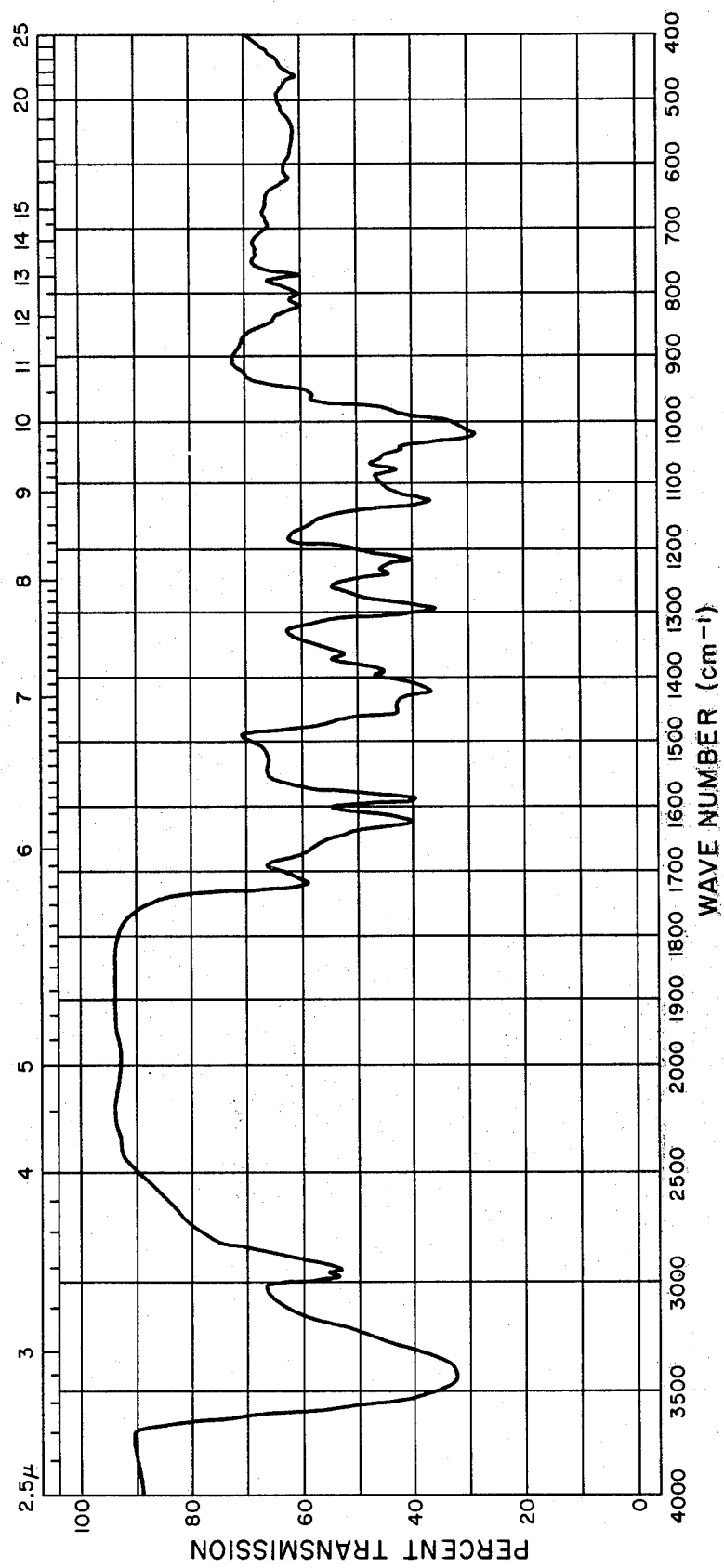
FIG. 2 shows the infrared absorption spectrum of baumycin $A_1$ when pelleted in potassium bromide.
Figure 3:
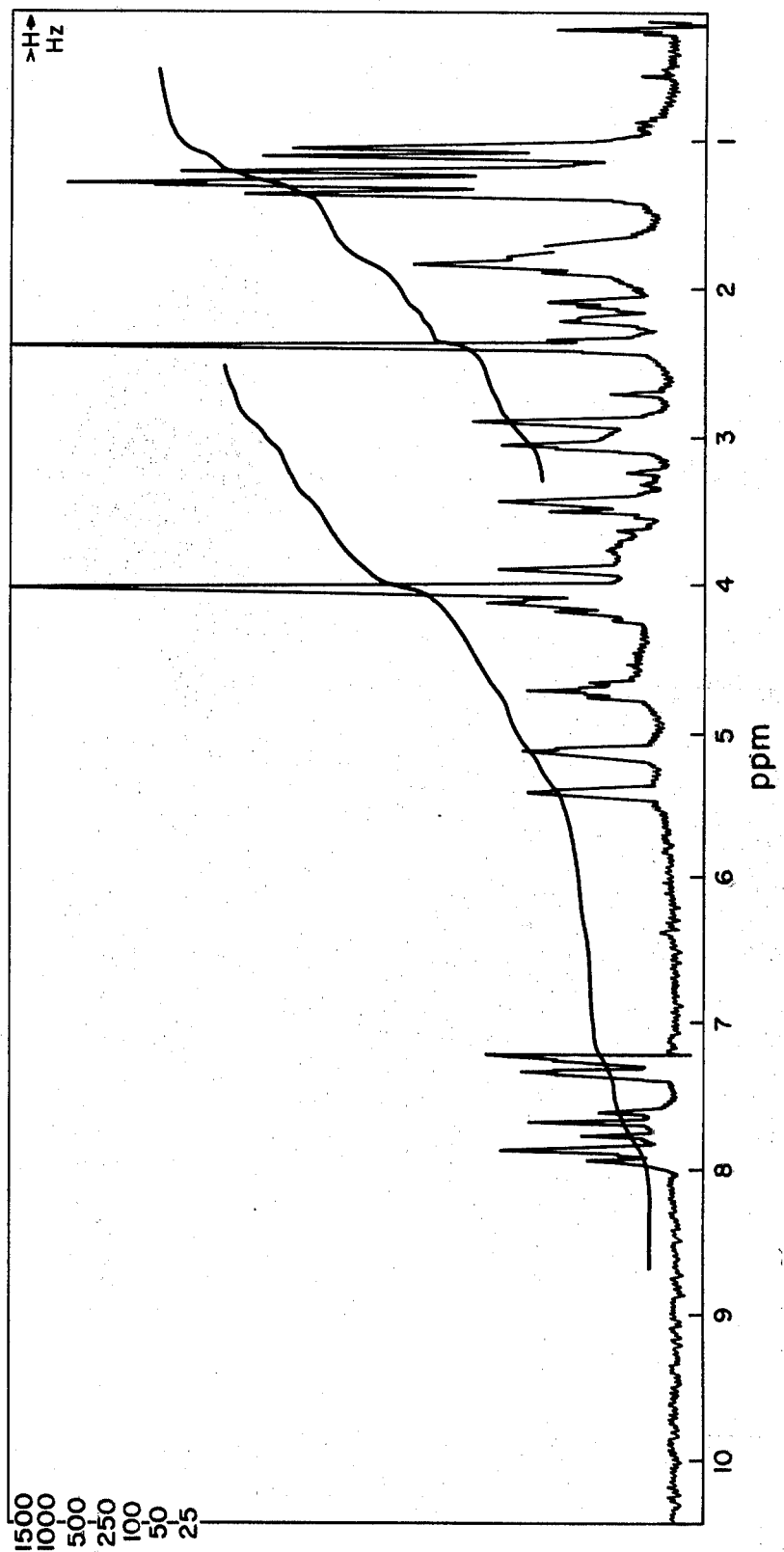
FIG. 3 shows the NMR spectrum of baumycin $A_1$ in $CDCl_3$ (100 MHz).
Figure 4:
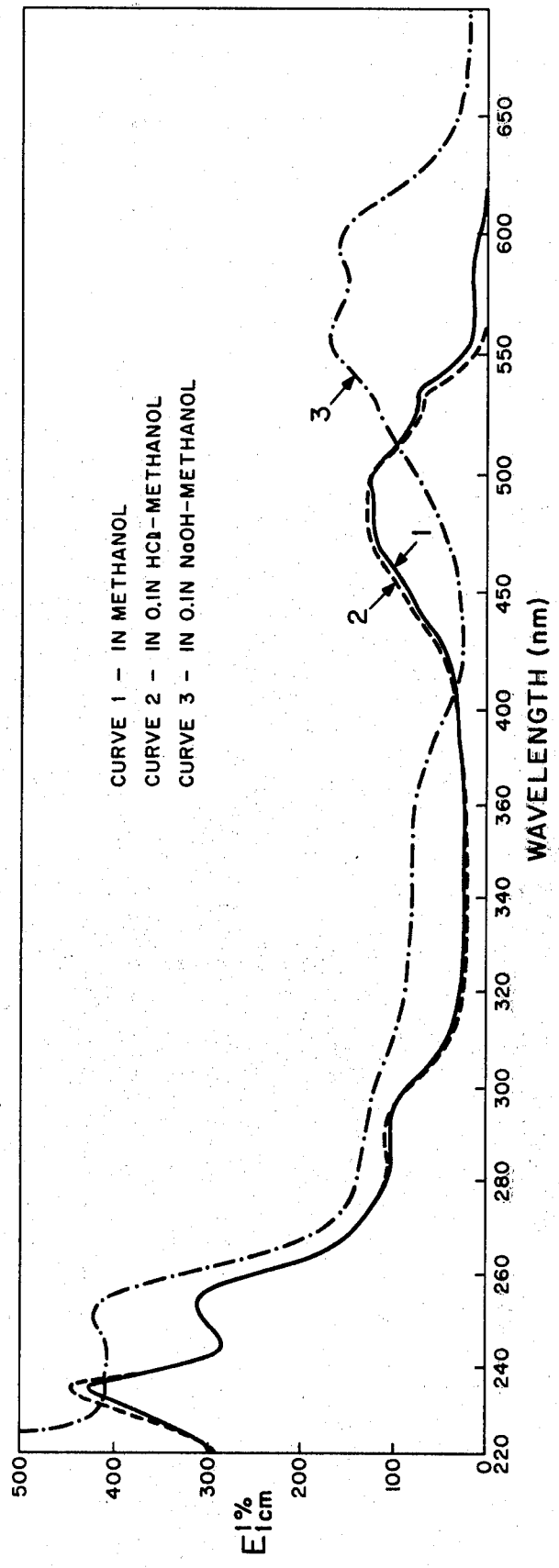
FIG. 4 shows the ultraviolet and visible light absorption spectrum of baumycin $A_2$ in methanol.
Figure 5:
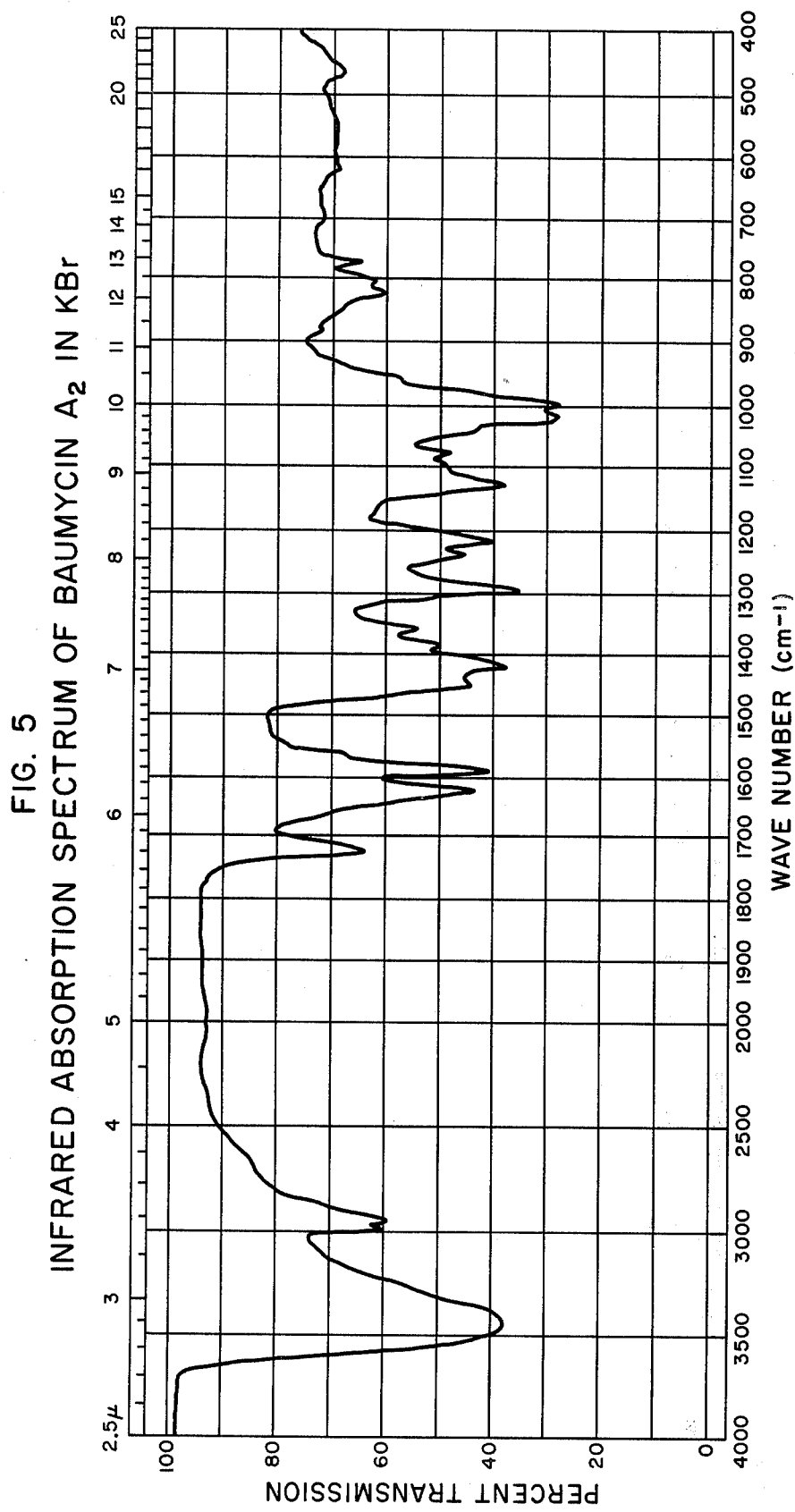
FIG. 5 shows the infrared absorption spectrum of baumycin $A_2$ when pelleted in potassium bromide.
Figure 6:
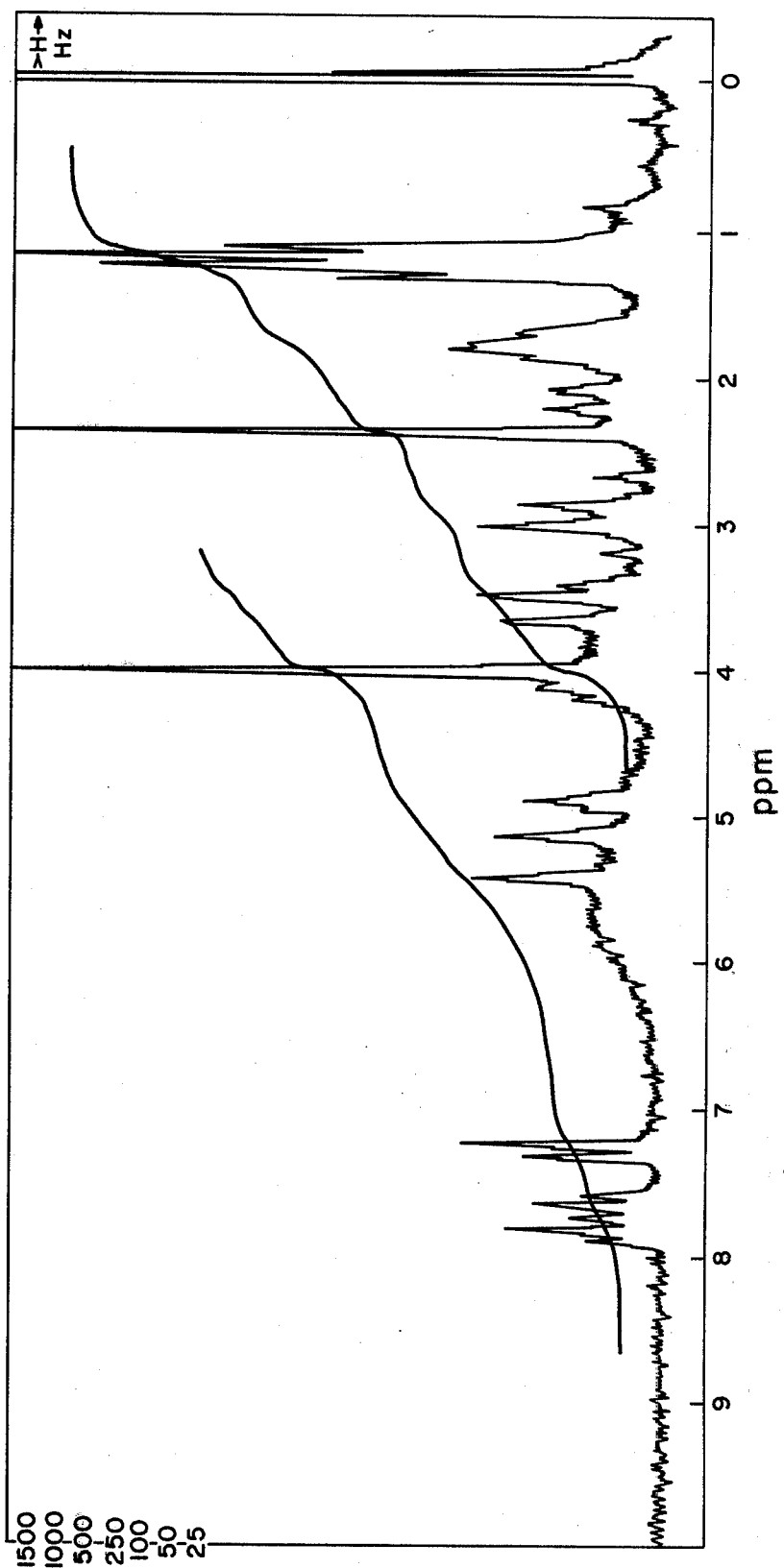
FIG. 6 shows the NMR spectrum of baumycin $A_2$ in $CDCl_3$ (100 MHz).

|  |  | -continued |  |
|---|---|---|---|
|  |  | chloride and chloroform. Insoluble in water, n-hexane, cyclohexane and petroleum ether. |  |
| $R_f$ values** |  |  |  |
| *C:M = 10:1 |  | 0.25 | 0.08 |
| C:M:B = 7:3:3 |  | 0.39 | 0.28 |
| C:M:F = 90:10:1 |  | 0.26 | 0.17 |
| C:M:A = 80:20:4 |  | 0.74 | 0.64 |
| Reaction |  | Acidic aqueous and methanol solution is red and turns to reddish purple in alkaline state. Baumycin $A_1$ and $A_2$ give positive ninhydrin reaction, and do not reduce Fehling solution. |  |
| UV and visible absorption spectra and max $(E_{1cm}^{1\%})$ in MeOH (curve 1) |  | Fig. 1<br>234.5 (452), 252.5 (327),<br>289 (120), 478 (127),<br>497 (128), 532 (76) | Fig. 4<br>234.5 (427), 252.5 (311),<br>289 (108), 478 (125),<br>497 (128), 532 (84) |
| in 0.1N HCl-MeOH (curve 2) |  | 234.5 (459), 252.5 (326),<br>289 (121), 479 (133),<br>497 (133), 532 (78) | 234.5 (447), 252.5 (311),<br>289 (111), 478 (131),<br>497 (131), 532 (70) |
| in 0.1N NaOH-MeOH (curve 3) |  | 250.5 (416), 350 (83),<br>558 (164), 597 (152) | 250.5 (421), 350 (80),<br>558 (170), 596 (164) |
| Infrared absorption spectrum (KBr) |  | Fig. 2 | Fig. 5 |
| NMR spectrum (PMR) |  | Fig. 3 | Fig. 6<br>(100 MHz, in $CDCl_3$) |
| ***$C^{13}$ NMR spectrum |  | Characteristic C-1" peak at 106.7 ppm | Characteristic C-1" peak at 101.6 ppm |

*C = chloroform, M = methanol, B = benzene, F = formic acid, A = acetic acid
**TLC condition: silicic acid thin layer 60F$_{254}$ (Merck Co.), 23° C.
***Spectrum measured on Varian XL100 instrument at 25.2 MHz. Internal reference is $CDCl_3$ for baumycin $A_1$ and TMS for baumycin $A_2$. Samples: $A_1$ = 27 mg./0.5 ml. $CDCl_3$; $A_2$ = 44 mg./0.6 ml. $CDCl_3$.

Figure 7:
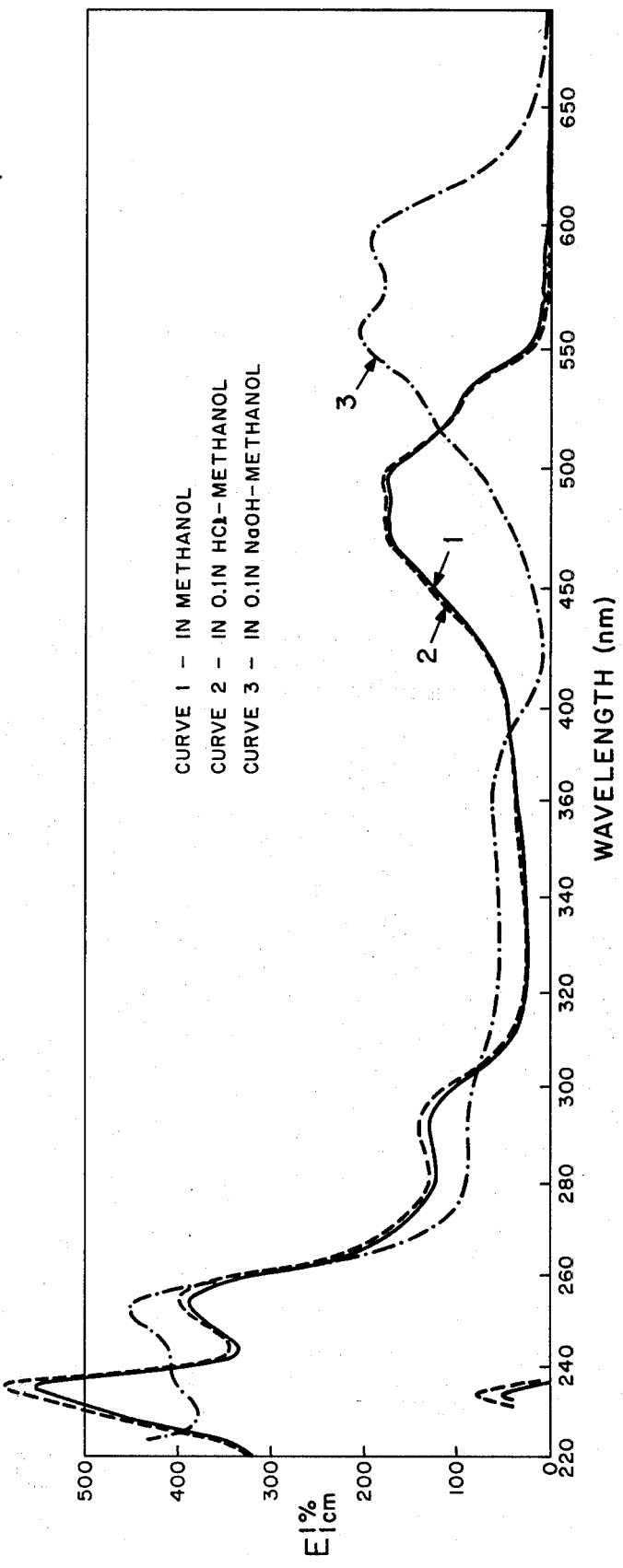
FIG. 7 shows the ultraviolet and visible light absorption spectrum of baumycin $B_1$ in methanol.
Figure 8:
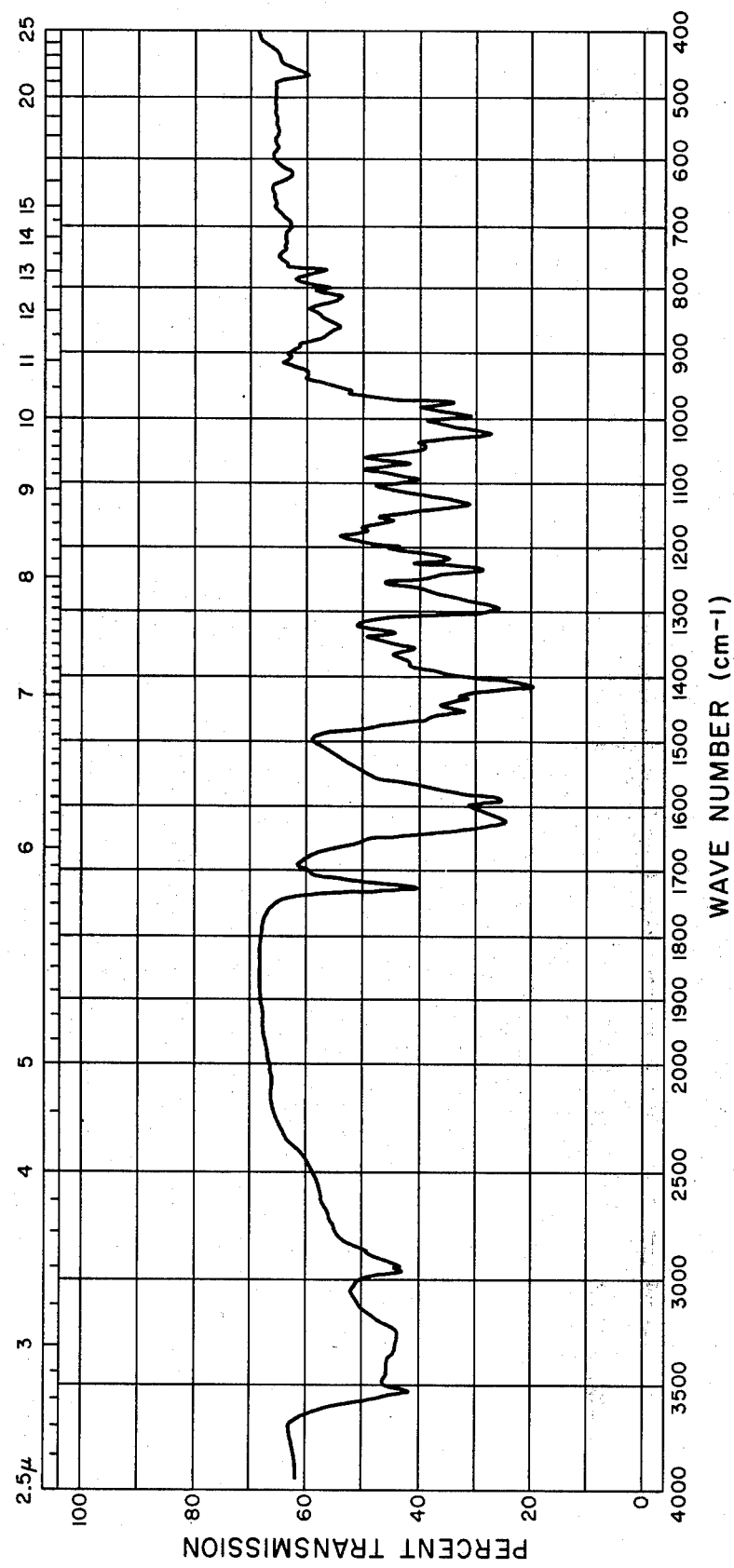
FIG. 8 shows the infrared absorption spectrum of baumycin $B_1$ when pelleted in potassium bromide.
Figure 10:
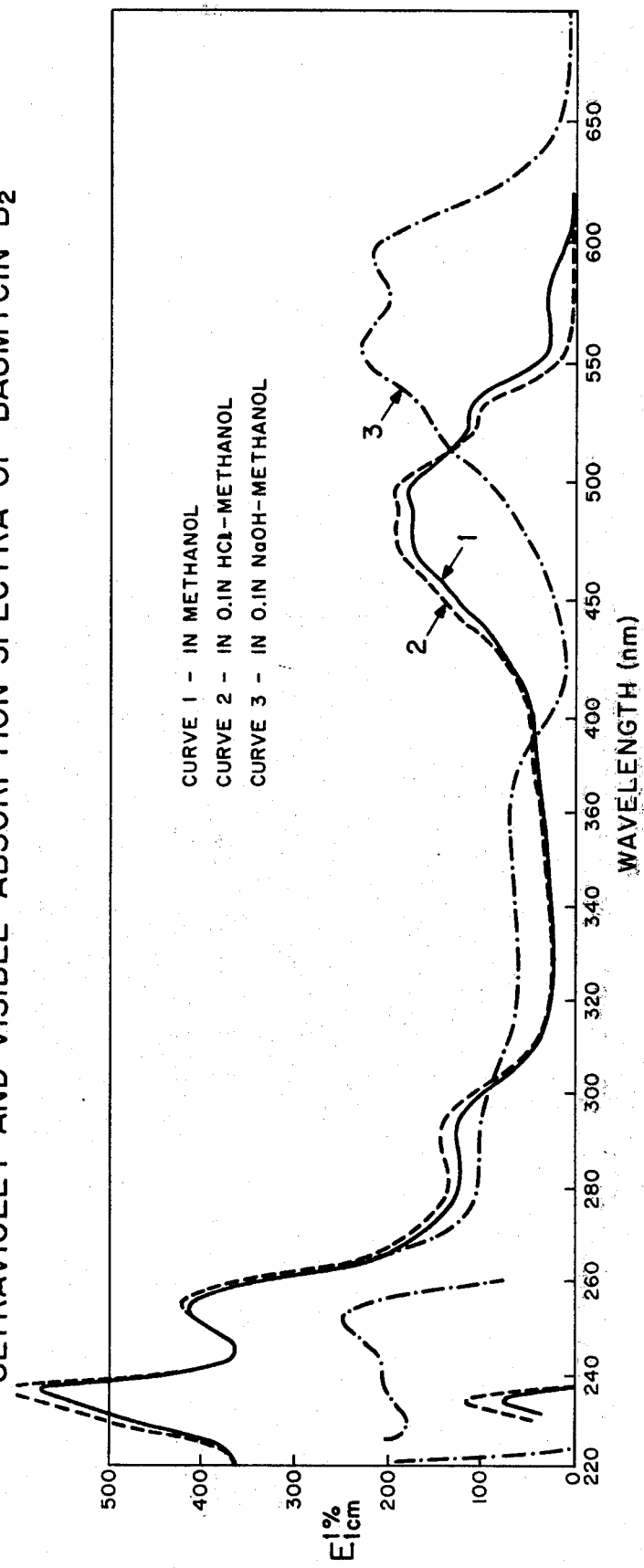
FIG. 10 shows the ultraviolet and visible light absorption spectrum of baumycin $B_2$ in methanol.
Figure 11:
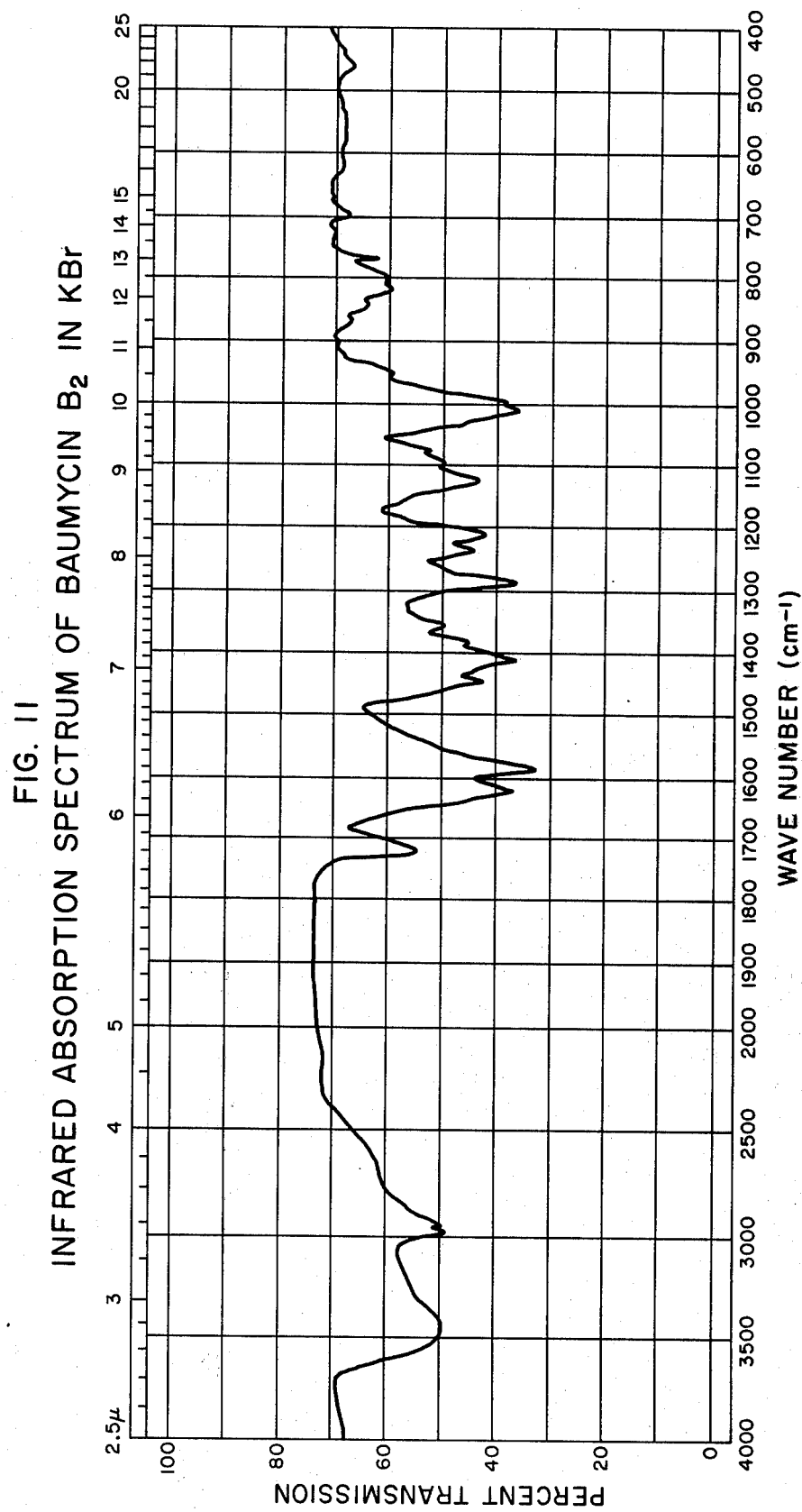
FIG. 11 shows the infrared absorption spectrum of baumycin $B_2$ when pelleted in potassium bromide.

| Baumycin |  | $B_1$ |  |  |  | $B_2$ |  |  |
|---|---|---|---|---|---|---|---|---|
| Appearance |  | Weakly basic amorphous red powder |  |  |  |  |  |  |
| Elementary analysis | C | H | N | O | C | H | N | O |
| Found | 57.32 | 6.45 | 2.01 | 32.58 | 56.59 | 5.96 | 1.92 | 31.91 |
| Calcd. | 59.38 | 6.01 | 2.04 | 32.57 | 59.38 | 6.01 | 2.04 | 32.57 |
| Empirical formula |  |  |  | $C_{34}H_{41}NO_{14}$ |  |  |  |  |
| Molecular weight |  |  |  | 687.7 |  |  |  |  |
| Melting point (° C.) |  | 181–189 |  |  |  | 197–201 |  |  |
| Specific rotation $[\alpha]_D^{20}$ |  | + 170° |  |  |  | + 170° |  |  |
|  |  |  | ($CHCl_3$ : MeOH = 1 : 1, C = 0.1) |  |  |  |  |  |
| Solubility |  | Soluble in acidic water, methyl cellosolve, methanol, ethanol, n-propanol and n-butanol. Insoluble in water, ethyl acetate, acetone, methylene chloride, chloroform, carbon tetrachloride, benzene, toluene, ethyl ether and n-hexane, except that baumycin $B_2$ is soluble in water. |  |  |  |  |  |  |
| $R_f$ values** |  |  |  |  |  |  |  |  |
| *C:M = 10:1 |  | 0.07 |  |  |  | 0.01 |  |  |
| C:M:B = 7:3:3 |  | 0.39 |  |  |  | 0.14 |  |  |
| C:M:F = 90:10:1 |  | 0.18 |  |  |  | 0.10 |  |  |
| C:M:A = 80:20:4 |  | 0.64 |  |  |  | 0.30 |  |  |
| Reaction |  | Acidic aqueous and methanol solution is red and turns to reddish purple in alkaline state. Baumycin $B_1$ and $B_2$ give positive ninhydrin reaction, and do not reduce Fehling solution. |  |  |  |  |  |  |
| UV and visible absorption spectra and max $(E_{1cm}^{1\%})$ in MeOH (curve 1) |  | Fig. 7<br>234.5 (552), 253 (385),<br>290 (132), 476 (179),<br>495 (181), 530 (101) |  |  |  | Fig. 10<br>234 (575), 252 (414),<br>290 (130), 478 (176),<br>495 (183), 530 (120) |  |  |
| in 0.1N HCl-MeOH (curve 2) |  | 234 (580), 253 (397),<br>290 (140), 476 (182),<br>495 (184), 530 (100) |  |  |  | 234 (616), 253 (419),<br>290 (145), 476 (195),<br>494 (191), 529 (105) |  |  |
| in 0.1N NaOH-MeOH (curve 3) |  | 251 (453), 350 (65),<br>556 (206), 594 (195) |  |  |  | 251 (499), 350 (74),<br>556 (231), 594 (218) |  |  |
| Infrared absorption spectrum |  | Fig. 8 |  |  |  | Fig. 11 |  |  |

Figure 9:
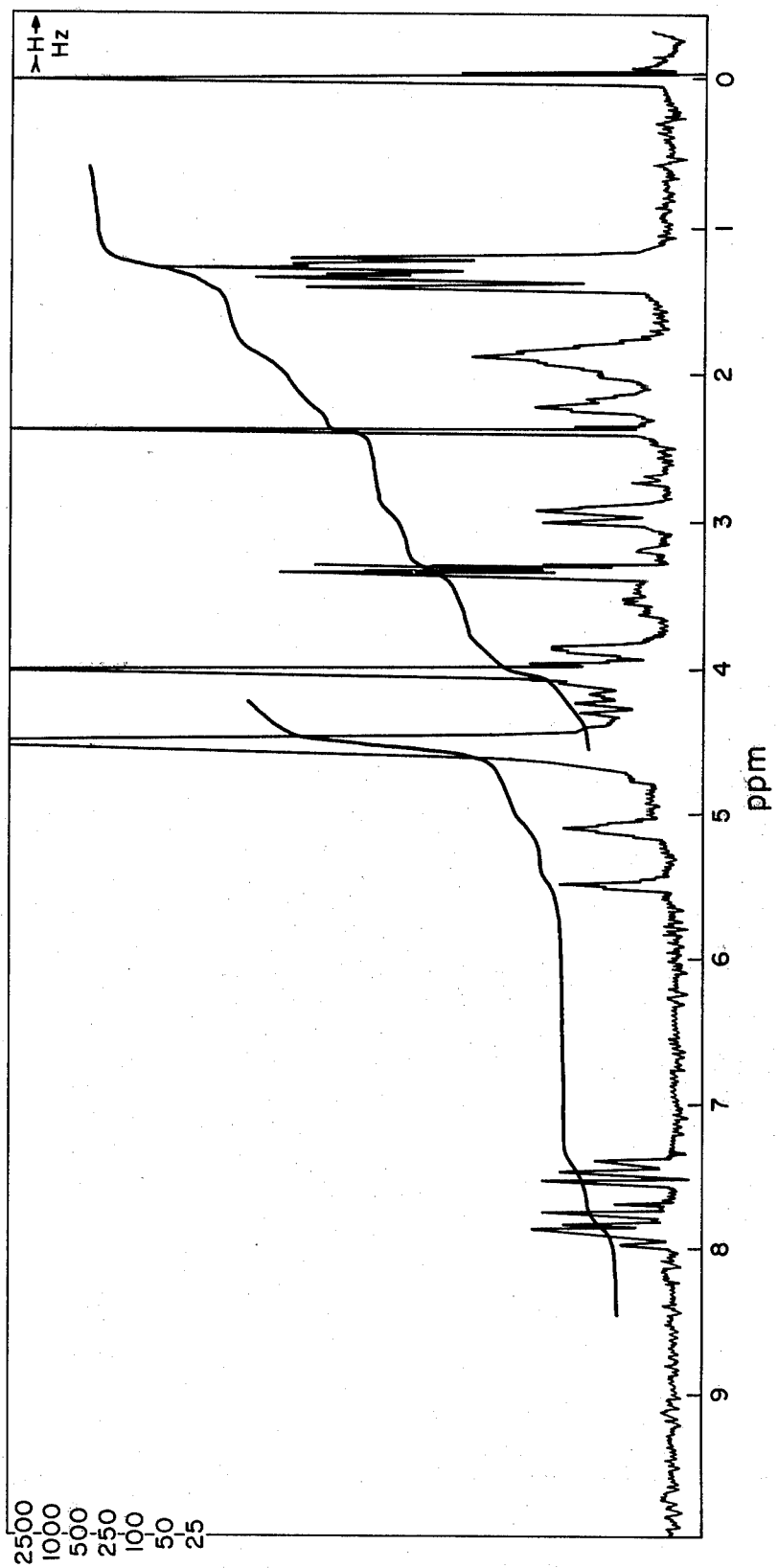
FIG. 9 shows the NMR spectrum of baumycin $B_1$ in a mixture of $CDCl_3$ and $CD_3OD$ (100 MHz).
Figure 12:
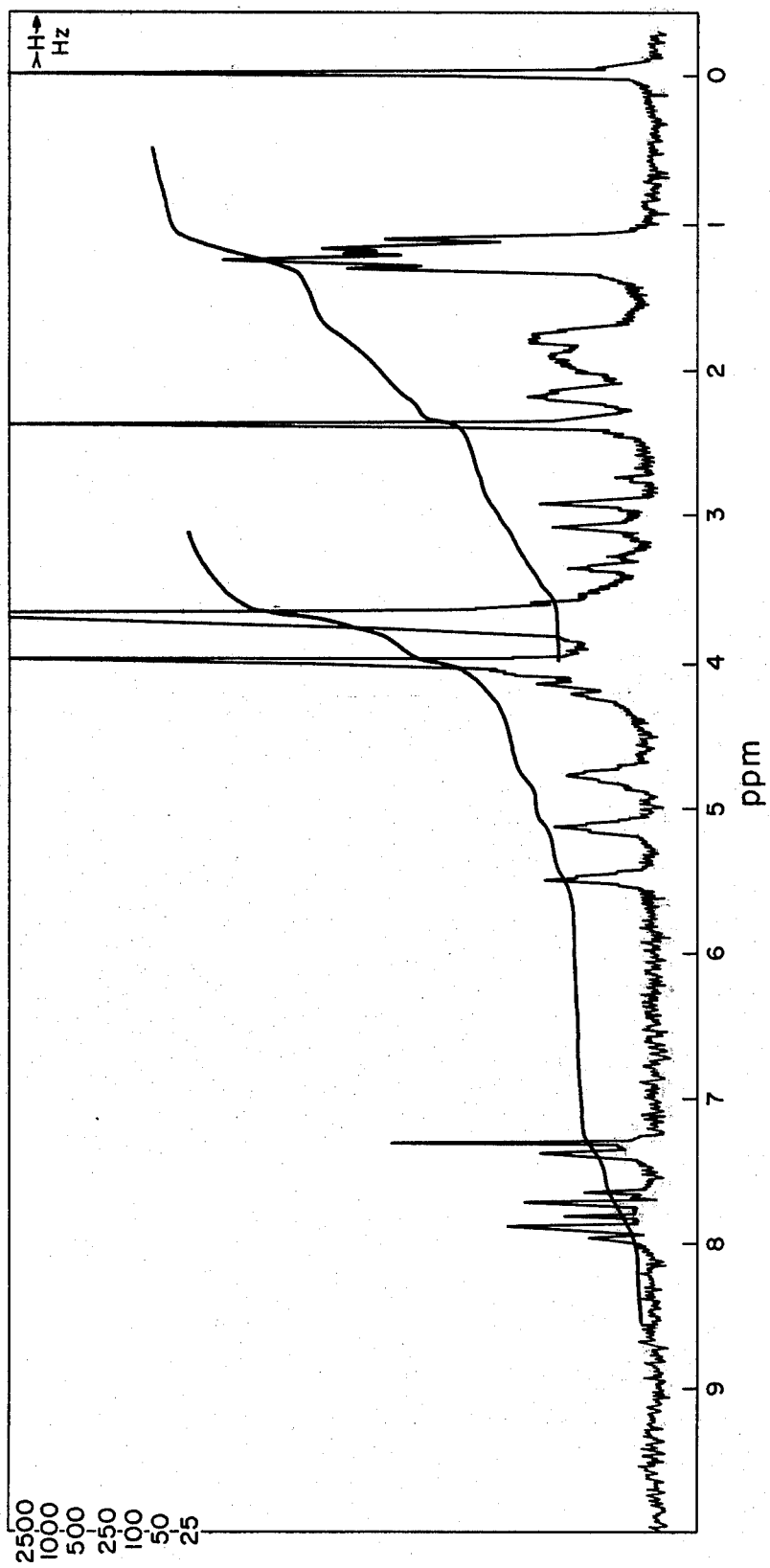
FIG. 12 shows the NMR spectrum of baumycin $B_2$ in a mixture of $CDCl_3$ and $CD_3OD$ (100 MHz).

| (KBr) | | |
|---|---|---|
| NMR spectrum | Fig. 9 | Fig. 12 |
| (PMR) | (100 MHz, in CDCl$_3$ and CD$_3$OD mixture) | |
| ***C$^{13}$ NMR spectrum | Characteristic C-1″ peak at 107.1 ppm | Characteristic C-1″ peak at 102.1 ppm |

°C = chloroform, M = methanol, B = benzene, F = formic acid, A = acetic acid
**TLC condition: silicic acid thin layer 60F$_{254}$ (Merck Co.), 23° C.
***Spectrum measured on Varian XL100 instrument at 25.2 MHz. Internal reference is TMS. Samples: B$_1$ = 45 mg./0.6 ml. CDCl$_3$:methanol (5:1); B$_2$ = 30 mg./0.6 ml. CDCl$_3$:methanol (1:1).

Structure Determination

The structures of baumycin A$_1$, A$_2$, B$_1$ and B$_2$ in the present invention were determined as follows: On hydrolysis with 0.1N hydrochloric acid for 30 min. at 85° C., baumycin A$_1$, A$_2$, B$_1$ and B$_2$ give daunomycinone and daunosamine, and daunomycin is obtained from the above baumycin components on partial hydrolysis with 1% sulfuric acid for 15 min. at 32° C. Physicochemical properties such as NMR, mass and infrared absorption spectra, melting point and R$_f$ values on thinlayer of daunomycinone, daunosamine and daunomycin obtained from baumycin A and B by acid hydrolysis coincided fully with those of authentic daunomycin. (Journal of American Chemical Society, 86, 5334–5335, 5335–5336 (1964)).

Further elucidation of the structures of baumycin A$_1$ and A$_2$ in the present invention was carried out as follows: The hydrogenolysis of baumycin A$_2$ with Pd/BaSO$_4$ in methanol gave an aglycone portion and a sugar moiety. From analysis of PMR and mass spectral data, the aglycone was determined to be 7-deoxydaunomycinone. With regard to the sugar moiety of baumycin A$_1$ and A$_2$, the tetracetyl derivative, which is obtained by the treatment of either moiety (i.e. that of A$_1$ or A$_2$) with acetic anhydride in pyridine, was analyzed by PMR and CI (chemical ionization) mass spectra and the following structure proposed:

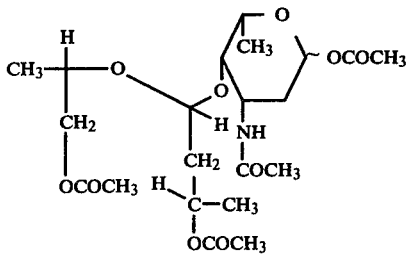

Figure 13:
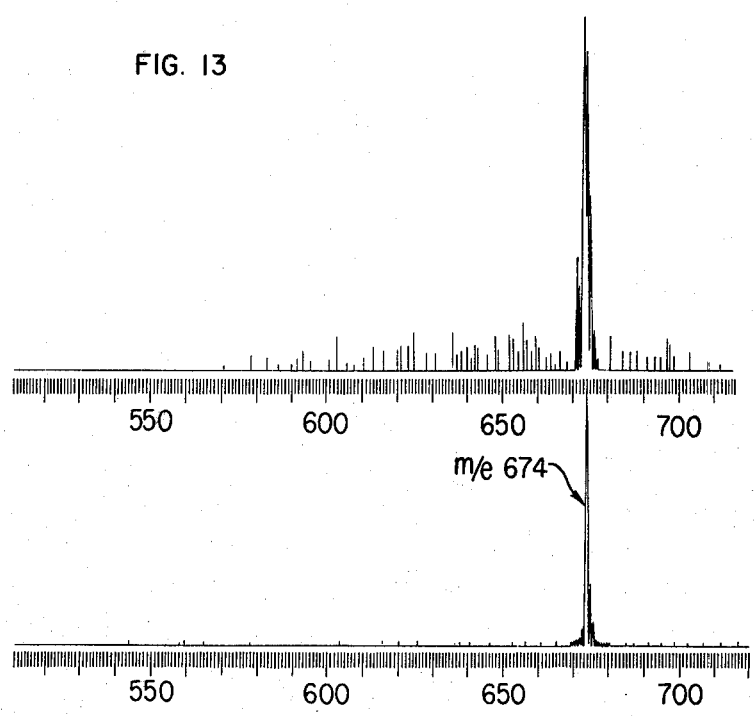
FIG. 13 shows the field desorption mass spectrum of baumycin $A_1$ (emitter current: 11 mA).
Figure 14:
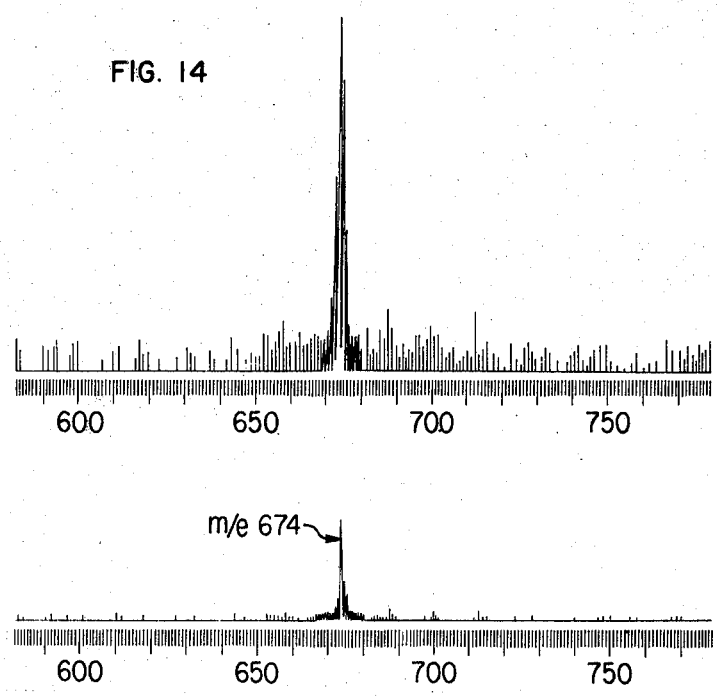
FIG. 14 shows the field desorption mass spectrum of baumycin $A_2$ (emitter current: 12 mA).

To further confirm the structures of baumycin A$_1$ and A$_2$, the molecular ion peak of each was determined by the recently developed FD (field desorption) mass spectrum analysis and was found to be m/e = 674 (M + 1) as shown in FIG. 13 and FIG. 14. Accordingly, the molecular formula for both baumycin A$_1$ and A$_2$ is C$_{34}$H$_{43}$NO$_{13}$. In view of the differences in melting points, specific rotations, thin layer chromatography R$_f$ values and C$^{13}$NMR peaks, baumycin A$_1$ and A$_2$ have been determined to be stereoisomers of each other.

The structures of baumycin B$_1$ and B$_2$ were determined as follows: Hydrogenolysis of baumycin B$_1$ with Pd/BaSO$_4$ in methanol gave an aglycone portion and a sugar moiety. From analysis of the PMR and mass spectral data, the aglycone portion was determined to be 7-deoxydaunomycinone. With regard to the sugar moiety, the diacetyl derivative thereof, which is obtained by treatment of each sugar moiety with acetic anhydride in pyridine, was analyzed by PMR and CI mass spectra and the following structure proposed:

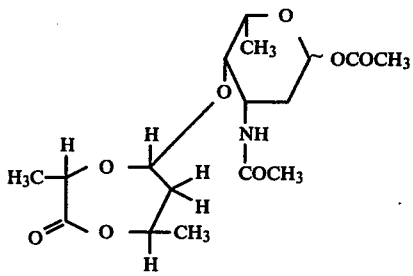

Figure 15:
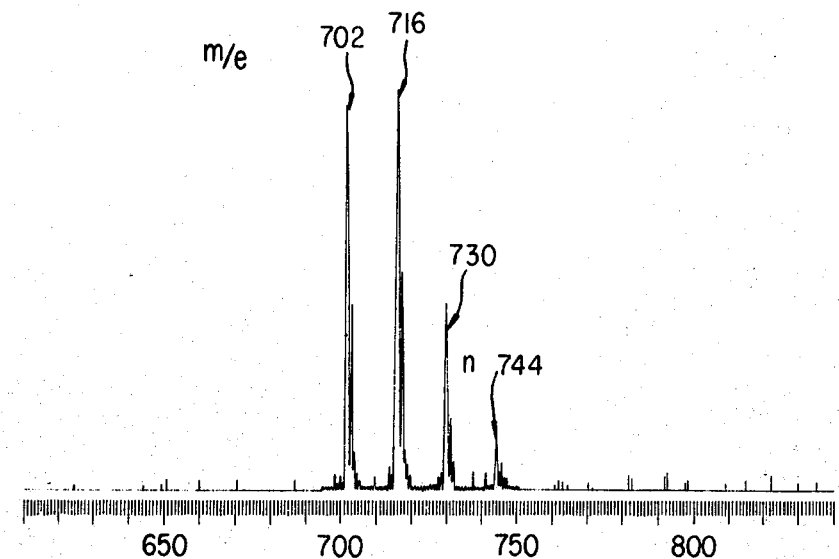
FIG. 15 shows the field desorption mass spectrum of baumycin $B_1$ methyl ester derivative (emitter current: 14 mA).
Figure 16:
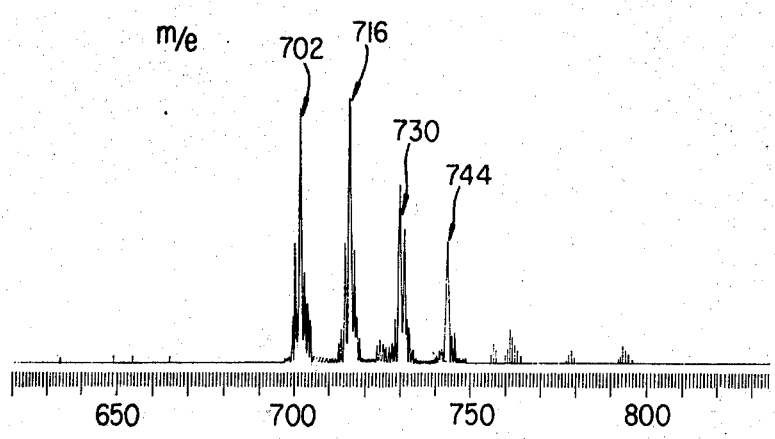
FIG. 16 shows the field desorption mass spectrum of baumycin $B_2$ methyl ester derivative (emitter current: 14 mA).

To further confirm the structures of baumycin B$_1$ and B$_2$, the molecular ion peak was determined for each by FD mass spectrum. Since the ion peak could not be obtained from baumycin B$_1$ and B$_2$ per se, their methyl ester derivative obtained by treatment with diazomethane was analyzed and showed a molecular ion peak at m/e = 702 (M+1) as indicated in FIG. 15 and FIG. 16. The peaks at m/e = 716, 730 and 744 shown in FIGS. 15 and 16 indicate the methylation of the amino residues in daunosamine. While baumycin B$_1$ and B$_2$ thus have the same molecular formula, it has been established from differences in their melting points, thin layer chromatography R$_f$ values and C$^{13}$ NMR peaks that they are stereoisomers of each other.

Summarizing the results of the above work, baumycin A$_1$ and A$_2$ have the general structure

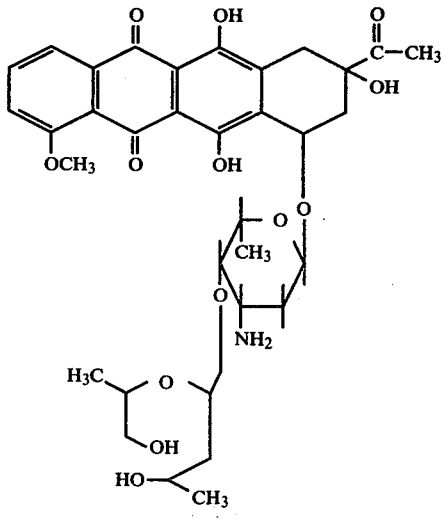

while baumycin B$_1$ and B$_2$ have the general structure

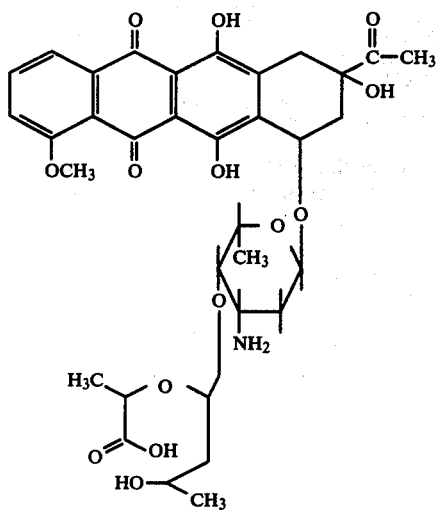

As mentioned above baumycins $A_1$ and $A_2$ and $B_1$ and $B_2$ are stereoisomers of each other and can be easily distinguished by differences in such physical properties as melting points, specific rotation ($A_1$ and $A_2$), thin layer $R_f$ values and $C^{13}$NMR peaks.

It will be readily seen from the above structures that baumycin $A_1$, $A_2$, $B_1$ and $B_2$ are novel anthracycline glycoside antibiotics which contain the same aglycone and the same amino sugar (i.e. daunosamine) as daunomycin but which differ from daunomycin in having the additional novel sugar moieties shown above. The baumycin antibiotics of the present invention have also been differentiated by the present inventors from known anthracycline antibiotics by $R_f$ value comparisons using silica gel thin layer chromatography with various solvent systems.

Antibiotic Activity of Baumycin

Baumycin $A_1$, $A_2$, $B_1$ and $B_2$ exhibit antimicrobial activities against various kinds of microorganisms. The minimum inhibitory concentration of the present antibiotics as determined by the broth dilution method are shown in Table 1.

Table 1

| Antimicrobial spectrum of baumycin $A_1$, $A_2$, $B_1$ and $B_2$ | | | | |
|---|---|---|---|---|
| | Minimum inhibitory concentration (mcg./ml) | | | |
| Test organism | BM-$A_1$ | BM-$A_2$ | BM-$B_1$ | BM-$B_2$ |
| *Staph. aureus* FDA209P | 1.56 | 3.12 | 50 | 100 |
| *Staph. aureus* Smith | 0.78 | 1.56 | 50 | 50 |
| *B. subtilis* ATCC 6633 | 0.78 | 3.12 | 100 | >100 |
| *B. cereus* ATCC 9634 | 1.56 | 3.12 | 100 | >100 |
| *B. megarterium* NRRL B-938 | 1.56 | 6.25 | 100 | >100 |
| *Sarcina lutea* ATCC 9341 | 0.78 | 3.12 | 50 | 25 |
| *Micrococcus flavs* | 0.78 | 1.56 | 50 | 50 |
| *Coryne. bovis* 1810 | 1.56 | 6.25 | 50 | 50 |
| *Ps. fluorescens* NIHJB-254 | >100 | 100 | 100 | >100 |
| *Proteus morganii* | >100 | >100 | >100 | >100 |
| *Mycobacterium smegmatis* ATCC 607 | 6.25 | 12.5 | 100 | >100 |
| *Candida albicans* IAM 4905 | 100 | 100 | 100 | >100 |
| *Candida tropicalis* | 100 | 100 | 100 | >100 |

BM: baumycin

As shown above, baumycin $A_1$, $A_2$, $B_1$ and $B_2$ in the present invention possess antimicrobial activity, especially against gram-positive bacteria, and thus they are therapeutically useful in the treatment of animals, including man, for diphtheria, tuberculosis, pneumonia, tetanus and other infectious diseases caused by gram-positive bacteria.

Antitumor Activity of Baumycin

Baumycin $A_1$, $A_2$, $B_1$ and $B_2$ in the present invention show a marked antitumor activity with low toxicity in experimental animal tests and thus are therapeutically useful in inhibiting the growth of animal tumors. In particular, baumycin $A_1$, $A_2$, $B_1$ and $B_2$ showed marked inhibitory effects on mouse L-1210 leukemia. For example, $BDF_1$ mice were inoculated intraperitoneally with $1 \times 10^6$ L-1210 cells/mouse and 24 hrs. after inoculation the drug was intraperitoneally injected once daily for 10 days consecutively. On day 30, the % of prolongation of the survival time to control was as follows:

| Dose (mg./kg./day) | Prolongation of the survival time T/C (%) | | | |
|---|---|---|---|---|
| | BM-$A_1$ | BM-$A_2$ | BM-$B_1$ | BM-$B_2$ |
| 8 | | | 147 | 155 |
| 6 | | | 165 | 135 |
| 4 | | | 136 | 111 |
| 2 | | | 117 | 99 |
| 1 | | 167 | 105 | 99 |
| 0.5 | | 173 | 99 | |
| 0.25 | | 163 | 99 | |
| 0.125 | | 151 | 93 | |
| 0.06 | >300 | 141 | | |
| 0.03 | 187 | | | |
| 0.015 | 155 | | | |
| 0.008 | 131 | | | |
| 0.004 | 131 | | | |

Acute Toxicity

The $LD_{50}$ values upon intraperitoneal injection of the antibiotics of the present invention are shown in the following table.

| | $LD_{50}$ (mg./kg.) |
|---|---|
| BM-$A_1$ | 1.5–2.5 |
| BM-$A_2$ | 15–20 |
| BM-$B_1$ | 40–60 |
| BM-$B_2$ | 75–100 |

BM: baumycin

The Therapeutic Use of Baumycin

As mentioned above, the compounds baumycin $A_1$, $A_2$, $B_1$ and $B_2$ in the present invention are novel antibiotics, useful in both human and veterinary medicine, and also possess marked inhibitory action against animal malignant tumors, especially ascitic and solid tumors.

The compounds in the present invention form non-toxic acid addition salts with a variety of organic and inorganic salt-forming reagents and form non-toxic complexes with deoxyribonucleic acid. Thus, acid addition salts formed with such pharmaceutically acceptable acids as sulfuric, phosphoric, hydrochloric, acetic, propionic, oleic, palmitic, citric, succinic, tartaric, glutamic, pantothenic, etc. and non-toxic complexes with deoxyribonucleic acid can be employed in the same manner as the baumycin compounds per se. The salts are formed, isolated, purified and formulated by the methods generally employed in salt formation for antibiotics. In the case of the DNA complexes, DNA extracted from animals and microorganisms such as calf thymus, Hela cells, human and animal embryonic cells, yeasts, etc. can be used. Preparation of baumycin-DNA complexes can be carried out by methods described in the literature for preparing DNA complexes of other anthracycline antibiotics such as adriamycin, daunorubicin, etc. [see, for example, Nature, New Biol.

239:110 (1973) and Europ. J. Cancer 10:399(1974)]. For purposes of this invention, the baumycin compounds in the free base form are equivalent to their non-toxic acid addition salts and DNA-complexes.

According to another aspect of this invention, a method is provided for therapeutically treating a mammalian host affected by a gram-positive bacterial infection or an experimental animal host affected by a malignant tumor (e.g. a solid or ascitic-type tumor such as L-1210 leukemia) which comprises administering to said host an effective antibacterial or tumor-inhibiting dose of baumycin $A_1$, $A_2$, $B_1$ and $B_2$, or a mixture thereof, or a non-toxic acid addition salt or DNA-complex thereof.

According to another aspect of this invention, a pharmaceutical composition is provided which comprises an effective antibacterial or tumor-inhibiting amount of baumycin $A_1$, $A_2$, $B_1$ or $B_2$, or a mixture thereof, or a non-toxic acid addition salt or DNA-complex thereof, in combination with an inert pharmaceutically acceptable carrier or diluent. These compositions may be made up in any pharmaceutical form appropriate for parenteral administration.

Preparations according to the invention for parenteral administration include sterile aqueous or non-aqueous solutions, suspensions or emulsions. They may also be manufactured in the form of sterile solid compositions which can be dissolved in sterile water, physiological saline or some other sterile injectable medium immediately before use.

It will be appreciated that the actual preferred amounts of the baumycin antibiotic used will vary according to the particular compound being used, the particular composition formulated, the mode of application and the particular situa, host and disease being treated. In general the baumycin antibiotics are injected intraperitoneally, intravenously, subcutaneously or locally into animals. Many factors that modify the action of the drug will be taken into account by those skilled in the art, for example, body weight, diet, time of administration, route of administration, rate of excretion, condition of the patient, drug combinations, reaction sensitivities and severity of the disease. Administration can be carried out continuously or periodically within the maximum tolerated dose. Optimal application rates for a given set of conditions can be ascertained by those skilled in the art using conventional dosage determination tests in view of the above guidelines.

For use as an antibcacterial agent, the baumycin compositions are in general administered so that the concentration of active ingredient is greater than the minimum inhibitory concentration for the particular organism being treated.

The following examples are provided for illustrative purposes only and are not intended to limit the scope of the invention.

EXAMPLE 1

A nutrient medium having the following composition was prepared:

| Potato starch | 1 | % |
|---|---|---|
| Glucose | 1 | % |
| "Prorich" (Soybean powder) | 1.5 | % |
| $K_2HPO_4$ | 0.1 | % |
| $MgSO_4.7H_2O$ | 0.1 | % |
| NaCl | 0.3 | % |
| Mineral* | 0.125 | % (pH 7.4) |
| *Mineral $CuSO_4.5H_2O$ | 2.8 | g |

-continued

| $FeSO_4.7H_2O$ | 0.4 | g |
|---|---|---|
| $MnCl_2.4H_2O$ | 3.2 | g |
| $ZnSO_4.7H_2O$ | 0.8 | g |
| in 500 ml. of water | | |

Fifty ml. of this medium was sterilized at 120° C. for 15 min. in a 500 ml.-flask which was inoculated from an agar slant culture of *Streptomyces coeruleorubidus* ME 130-A4 by platinum loop.

Incubation proceeded for 72 hrs. at 28° C. on a rotary shaker (230 rpm). This is the seed culture, Seven liters of the following medium was prepared, and 50 ml. of the medium distributed and sterilized in a 500 ml.-flask was aseptically inoculated with 1 ml. of the above seed culture. Fermentation was carried out at 28° C. for 7 days on a rotary shaker (230 rpm).

| Sucrose | 4 | % |
|---|---|---|
| "Prorich" | 2.5 | % |
| (Soybean protein, Ajinomoto Co.) | | |
| NaCl | 0.25 | % |
| Calcium carbonate | 0.32 | % |
| Mineral* | 0.125 | % (pH 7.4) |
| *Mineral $CuSO_4.5H_2O$ | 1.25 | g |
| $MnCl_2.4H_2O$ | 1.25 | g |
| $ZnSO_4.7H_2O$ | 12.5 | g |
| in 500 ml. of water | | |

The cultured broth obtained was filtered to separate the culture filtrate and mycelium. The filtrate was extracted three times with 1/5 volume of chloroform. The mycelium was extracted three times with 2 l of acetone per 1 kg. of cake, and the resulting acetone extract was concentrated to half volume under reduced pressure.

The concentrate was extracted three times with 2 l of chloroform, combined with the chloroform solution which was obtained from the culture filtrate, and concentrated to dryness under reduced pressure. Ten g. of oil substance obtained was dissolved in 50 ml. of chloroform, and the precipitate formed by addition of 300 ml. of n-hexane was centrifuged for 5 mim. at 3000 rpm to remove impure substances soluble in n-hexane. The resulting precipitate (1.4 g.) was dissolved in 100 ml. of chloroform and extracted three times with 150 ml. of 0.01 M acetic acid to obtain acidsoluble substances. To the extract was added 2 M trishydroxyamino-methane solution to adjust to pH 8.5, and the solution was then extracted three times with 100 ml. of chloroform. There was obtained 230 mg. of red crude powder (baumycin complex) from the chloroform layer by concentration to dryness under reduced pressure.

EXAMPLE 2

The crude powder obtained as in Example 1 (230 mg.) was dissolved in 2 ml. of chloroform-methanol mixture (10:1), subjected to a column 65 cm. in length and 8 cm. in diameter filled with 80 g. of silicic acid and washed with chloroform-methanol mixture (10:1). The baumycin $A_1$ fraction was eluted first, followed successively by baumycin $A_2$, $B_1$ and $B_2$ using as the respective eluent 8:1, 5:1 and 2:1 mixtures of chloroform-methanol.

After each active fraction was pooled separately and concentrated to dryness under reduced pressure, each such fraction was applied to a column 25 cm. in length and 1.8 cm. in diameter filled with Sephadex LH-20 and washed with 3:1 toluene-methanol mixture. After concentrating each fraction obtained above, red powders of 10 mg. baumycin A₁, 18 mg. of baumycin A₂, 3 mg. baumycin B₁ and 1 mg. baumycin B₂ were obtained by the addition of n-hexane to the concentrate.

EXAMPLE 3

A nutrient medium having the following composition was prepared:

| | | |
|---|---|---|
| Potato starch | 2 | % |
| Glucose | 2 | % |
| Yeast extract (Daigo Eyo Co.) | 0.5 | % |
| NaCl | 0.25 | % |
| Calcium carbonate | 0.32 | % |
| Soya meal (Nishin Oil KK) | 2 | % |
| Mineral* | 0.2 | % (pH 7.4) |

*Mineral is same as in Example 1.

Eight liters of the above medium were prepared of which 50 ml. each were distributed in 500 ml.-flasks, sterilized at 120° C. for 15 min. and inoculated with 1 ml. of the seed culture of *Streptomyces peuceticus subsp. carneus* ATCC 21354 prepared by the method in Example 1. Fermentation was carried out on a rotary shaker at 28° C. for 6 days. The cultured broth was filtered to separate the mycelium from the culture filtrate. Extraction with chloroform and acetone proceeded as in Example 1, and 10 g. of oily substance was obtained. The oily substance was dissolved in 100 ml. of methanol and 1.2 g. of precipitate was obtained after removing n-hexane-soluble substances by addition of 100 ml. of n-hexane. The red precipitate was dissolved in 100 ml. chloroform and extracted with 600 ml. of sodium acetate buffer (pH 3.0) to obtain an acid -soluble substance. After adding 0.5 M ethylenediaminetetraacetic acid to the extract to become 0.01M, the pH was adjusted to 8 with 4M sodium hydrochloride.

The active components in this aqueous solution were extracted four times with 200 ml. of chloroform, and then extracted twice with 500 ml. of n-butanol. The resulting chloroform- and n-butanol-layers were concentrated separately under reduced pressure, and 200 mg. of red powder, which consisted mainly of baumycin B₂ was obtained. This crude powder was dissolved in 5 ml. of chloroform-methanol, applied to a column 23 cm. in length and 3.0 cm. in diameter filled with 80 g. of silicic acid and washed with the 20:1 mixture of chloroform and methanol. Baumycin B₁ and B₂ were eluted successively with the 5:1 and 2:1 mixtures of chloroform and methanol. Fractions of baumycins B₁ and B₂ were concentrated separately under reduced pressure and 50 mg. of baumycin b₁ and 8 mg. of baumycin b₂ were obtained. The resulting baumycin B₁ and B₂ were recrystallized from methanol, and 31 mg. and 6.5 mg. of crystalline material were obtained, respectively. In this method, very little baumycin A₁ and A₂ are produced.

EXAMPLE 4

According to the general method of Examples 1 and 2, baumycin A₁, A₂, B₁ and B₂ were obtained as follows using the indicated Streptomyces strains:

| Strains | Baumycin obtained (mg.) | | | |
|---|---|---|---|---|
| | A₁ | A₂ | B₁ | B₂ |
| *Streptomyces peuceticus subsp. carneus* ATCC 21354 | 8 | 12 | 4 | 2 |
| *Streptomyces coeruleorubidus* ATCC 13740 | 16 | 21 | 8 | 3 |
| *Streptomyces peuceticus subsp. Caestus* NRRL B-5337 | 11 | 10 | 7 | 3 |
| *Streptomyces peuceticus* NRRL B-3826 | 10 | 5 | 1 | 3 |
| *Streptomyces coeruleorubidus* NRRL B-3045 | 26 | 17 | 5 | 6 |

We claim:

1. An anthracycline glycoside of the general formula

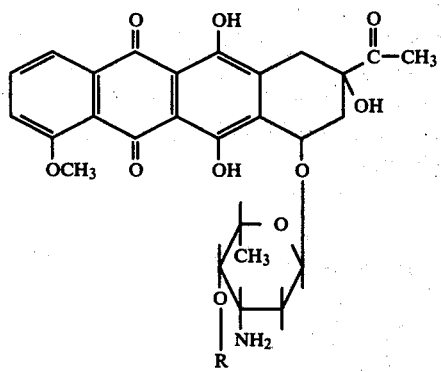

wherein R represents

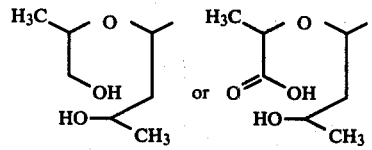

or a non-toxic acid addition salt or deoxyribonucleic acid complex thereof.

2. Baumycin A₁, the anthracycline glycoside isomer of the formula

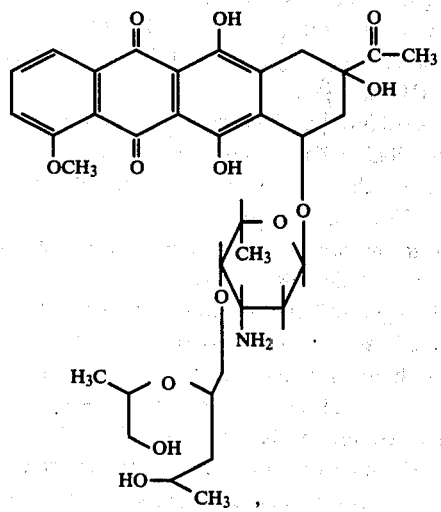

having the following characteristic properties:
(a) it has a melting point of 182°-185° C.;
(b) it has a specific rotation $[\alpha]_D^{20}$ + 150° (c = 0.1, CHCl₃);
(c) it exhibits the following R_f values as determined by silicic acid thin layer chromatography:

1. in the solvent system chloroform:methanol (10:1), $R_f = 0.25$;
2. in the solvent system chloroform:methanol:benzene (7:3:3), $R_f = 0.39$;
3. in the solvent system chloroform:methanol:formic acid (90:10:1), $R_f = 0.26$; and
4. in the solvent system chloroform:methanol:acetic acid (80:20:4), $R_f = 0.74$; and (d) it exhibits a characteristic $C^{13}$NMR absorption peak at 106.7 ppm relative to CDCl₃ when dissolved in CDCl₃ at a concentration of 27 mg. baumycin A₁/0.5 ml. CDCll₃ (Varian XL-100 instrument at 25.2 MHz), or a non-toxic acid addition salt or deoxyribonucleic acid complex thereof.

3. Baumycin A₁ as defined in claim 2.

4. Baumycin A₂, the anthracycline glycoside isomer of the formula

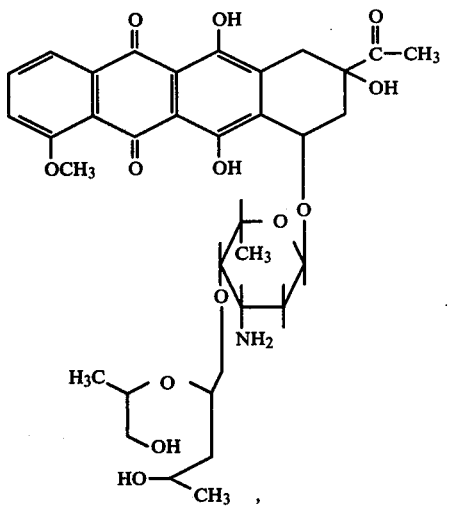

having the following characterisitc properties:
(a) it has a melting point of 185°-189° C.;
(b) is has a specific rotation $[\alpha]_D^{20} + 135°$ (c = 0.1, CHCl₃);
(c) it exhibits the following $R_f$ values as determined by silicic acid thin layer chromatography:
 1. in the solvent system chloroform:methanol (10:1), $R_f = 0.08$;
 2. in the solvent system chloroform:methanol:benzene (7:3:3), $R_f = 0.28$;
 3. in the solvent system chloroform:methanol:formic acid (90:10:1), $R_f = 0.17$; and
 4. in the solvent system chloroform:methanol:acetic acid (80:20:4), $R_f = 0.64$; and (d) it exhibits a characteristic $C^{13}$NMR absorption peak at 101.6 ppm relative to tetramethylsilane when dissolved in CDCl₃ at a concentration of 44 mg. baumycin A₂/0.6 ml. CDCl₃ (Varian XL-100 instrument at 25.2 MHz), or a non-toxic acid addition salt or deoxyribonucleic acid complex thereof.

5. Baumycin A₂ as defined in claim 4.

6. Baumycin B₁, the anthracycline glycoside isomer of the formula

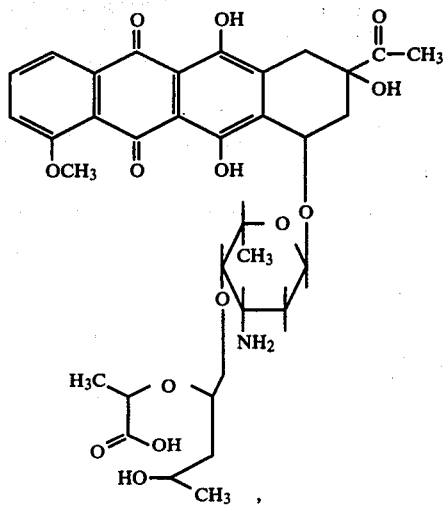

having the following characteristic properties:
(a) it has a melting point of 181°-189° C.;
(b) it exhibits the following $R_f$ values as determined by silicic acid thin layer chromatography:
 1. in the solvent system chloroform:methanol (10:1), $R_f = 0.07$;
 2. in the solvent system chloroform:methanol:benzene (7:3:3), $R_f = 0.39$;
 3. in the solvent system chloroform:methanol:formic acid (90:10:1), $R_f = 0.18$; and
 4. in the solvent system chloroform:methanol:acetic acid (80:20:4), $R_f = 0.64$; and (c) it exhibits a characteristic $C^{13}$NMR absorption peak at 107.1 ppm relative to tetramethylsilane when dissolved in CDCl₃:methanol (5:1) at a concentration of 45 mg. baumycin B₁/0.6 ml. solvent (Varian XL-100 instrument at 25.2 MHz), or a non-toxic acid addition salt or deoxyribonucleic acid complex thereof.

7. Baumycin B₁ as defined in claim 6.

8. Baumycin B₂, the anthracycline glycoside isomer of the formula

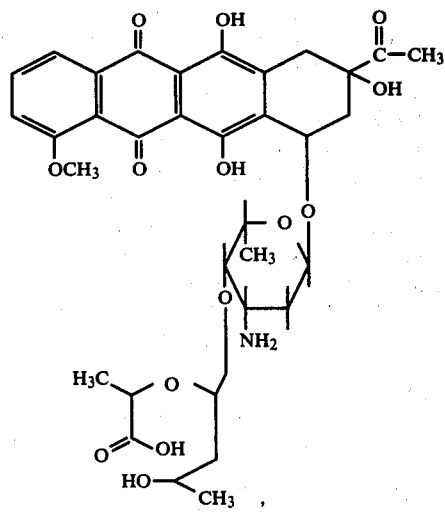

having the following characteristic properties:
(a) it has a melting point of 197°-201° C.;
(b) it exhibits the following $R_f$ values as determined by silicic acid thin layer chromatography:

1. in the solvent system chloroform:methanol (10:1), $R_f = 0.01$;
2. in the solvent system chloroform:methanol:benzene (7:3:3), $R_f = 0.14$;
3. in the solvent system chloroform:methanol: formic acid (90:10:1), $R_f = 0.10$; and
4. in the solvent system chloroform:methanol:acetic acid (80:20:4;1 ), $R_f = 0.30$; and (c) it exhibits a characteristic $C^{13}$ NMR absorption peak at 102.1 ppm relative to tetramethylsilane when dissolved in $CDCl_3$:methanol (1:1) at a concentration of 30 mg. baumycin $B_2$/0.6 ml. solvent (Varian XL-100 instrument at 25.2 MHz), or a non-toxic acid addition salt or deoxyribonucleic acid complex thereof.

9. Baumycin $B_2$ as defined in claim 8.

10. A pharmaceutical composition comprising an effective antibacterial amount of at least one antibiotic selected from the group consisting of baumycin $A_1$, $A_2$, $B_1$ or $B_2$, a non-toxic acid addition salt thereof, and a deoxyribonucleic acid complex thereof, in combination with an inert pharmaceutically acceptable carrier or diluent.

11. A pharmaceutical composition according to claim 10 wherein the active ingredient is baumycin $A_1$, or a non-toxic acid addition salt or deoxyribonucleic acid complex thereof.

12. A pharmaceutical composition according to claim 10 wherein the active ingredient is baumycin $A_2$, or a non-toxic acid addition salt or deoxyribonucleic acid complex thereof.

13. A pharmaceutical composition according to claim 10 wherein the active ingredient is baumycin $B_1$, or a non-toxic acid addition salt or deoxyribonucleic acid complex thereof.

14. A pharmaceutical composition according to claim 10 wherein the active ingredient is baumycin $B_2$, or a non-toxic acid addition salt or deoxyribonucleic acid complex thereof.

* * * * *